(12) United States Patent
Mazzio et al.

(10) Patent No.: US 8,802,161 B2
(45) Date of Patent: Aug. 12, 2014

(54) HERBAL COMPOSITION AND METHOD OF USE FOR THE TREATMENT OF CANCER

(75) Inventors: Elizabeth Anne Mazzio, Tallahassee, FL (US); Karam F Soliman, Tallahassee, FL (US)

(73) Assignee: Florida Agricultural and Mechanical University, Tallahassee, FL (US)

( * ) Notice: Subject to any disclaimer, the term of this patent is extended or adjusted under 35 U.S.C. 154(b) by 202 days.

(21) Appl. No.: 12/657,903

(22) Filed: Jan. 30, 2010

(65) Prior Publication Data

US 2010/0209388 A1 Aug. 19, 2010

Related U.S. Application Data

(63) Continuation-in-part of application No. 11/711,883, filed on Feb. 27, 2007, now abandoned, which is a continuation-in-part of application No. 11/233,279, filed on Sep. 20, 2005, now abandoned, which is a continuation-in-part of application No. 10/909,590, filed on Aug. 2, 2004, now abandoned.

(60) Provisional application No. 60/491,841, filed on Aug. 2, 2003, provisional application No. 60/540,525, filed on Jan. 29, 2004.

(51) Int. Cl.

| | |
|---|---|
| *A61K 36/00* | (2006.01) |
| *A61K 36/54* | (2006.01) |
| *A61K 36/71* | (2006.01) |
| *A61K 36/236* | (2006.01) |
| *A61K 36/324* | (2006.01) |
| *A61K 36/328* | (2006.01) |
| *A61K 36/484* | (2006.01) |
| *A61K 36/537* | (2006.01) |
| *A61K 36/8945* | (2006.01) |
| *A61K 36/704* | (2006.01) |
| *A61K 36/28* | (2006.01) |

(52) U.S. Cl.
CPC ............... *A61K 36/00* (2013.01); *A61K 36/54* (2013.01); *A61K 36/71* (2013.01); *A61K 36/324* (2013.01); *A61K 36/328* (2013.01); *A61K 36/236* (2013.01); *A61K 36/484* (2013.01); *A61K 36/537* (2013.01); *A61K 36/704* (2013.01); *A61K 36/8945* (2013.01); *A61K 36/28* (2013.01)
USPC ........... 424/725; 424/726; 424/739; 424/746; 424/748; 424/773; 424/777; 424/778

(58) Field of Classification Search
None
See application file for complete search history.

(56) References Cited

PUBLICATIONS

Mazzio, E. A., et al. Phytother. Res. (2009), 23; pp. 385-398; Published Online Oct. 9, 2008.*
Chen, X. et al. Phytother. Res. (2002), 16; pp. 199-209.*
Manna, S., K., et al. Clin. Cancer Res. (2007), 13; pp. 2290-2297.*
Adams, M. http://www.chlorellafactor.com/chlorella-spirulina-19.html; available at least by Dec. 2007; accessed online Mar. 28, 2012.*
Yi, T., et al. Mol. Cancer Ther. (2008), 7; pp. 1789-1796.*
Wenzel, U., et al. Apoptosis (2005), 10; pp. 359-368.*

* cited by examiner

*Primary Examiner* — Kevin S Orwig

(57) ABSTRACT

The invention describes a nutraceutical composition and method for preventing/treating cancer or augmenting chemotherapy in advanced stage malignancies; comprised of [1] tumoricidal herbs; beth root, galbanum, gromwell root, wild yam, balm of gilead bud, frankincense, [2] an antiproliferative herb; speranskia [3] a natural lactic acid dehydrogenase (LDH) inhibitor, 2',3,4'5,7-pentahydroxyflavone or cinnamon, [4] alkalizing agents: calcium, magnesium, potassium or bicarbonate salts, barley grass, chlorella and spirulina [5] at least one quinone and [6] at least one agent capable of maximizing oxidative mitochondrial function preferably riboflavin, 6,7-Dimethyl-8-(1-D-ribityl)lumazine, ribitol, 5,6-dimethylbenzimidazole, tetrahydrobiopterin and a pharmaceutically acceptable carrier.

7 Claims, 8 Drawing Sheets

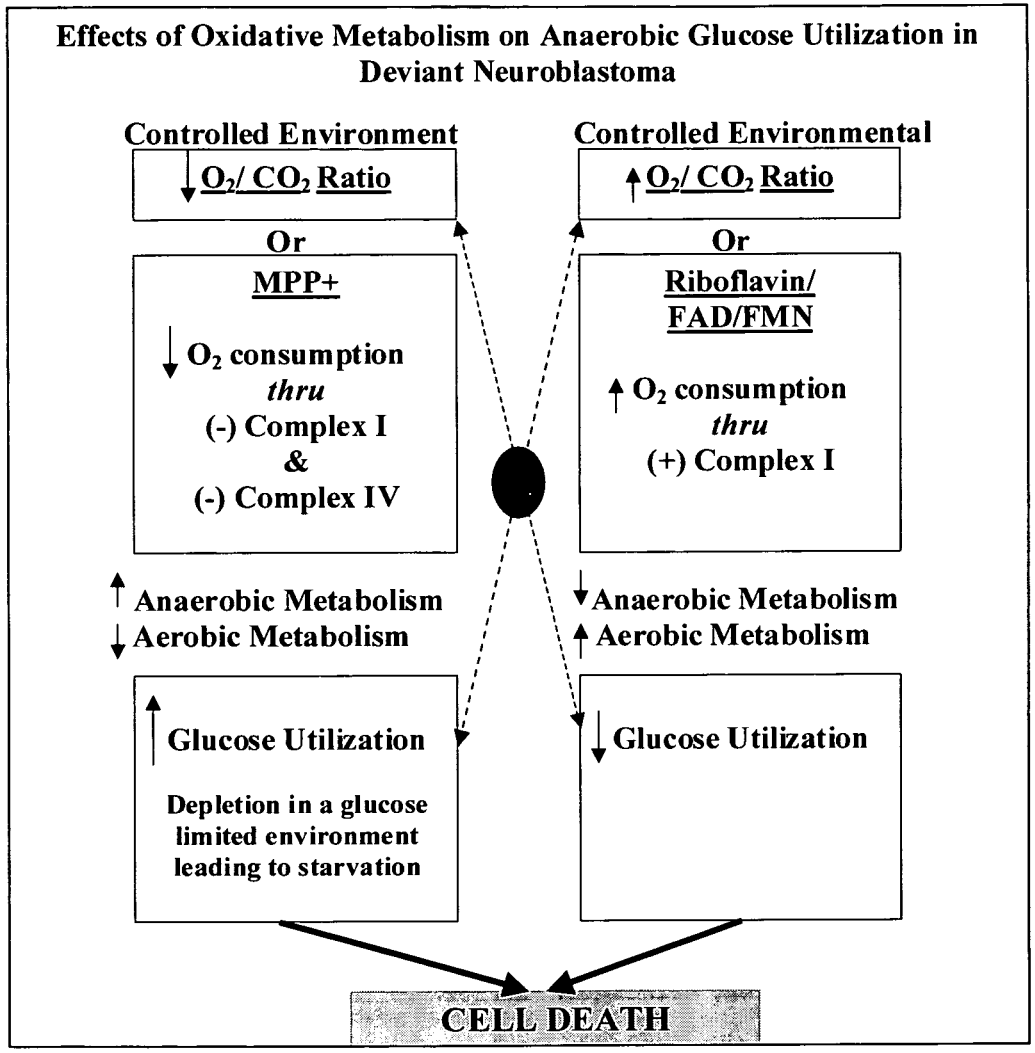
Figure 1 - Mazzio and Soliman, Biochem Pharmacol. 67:1167-84, 2004

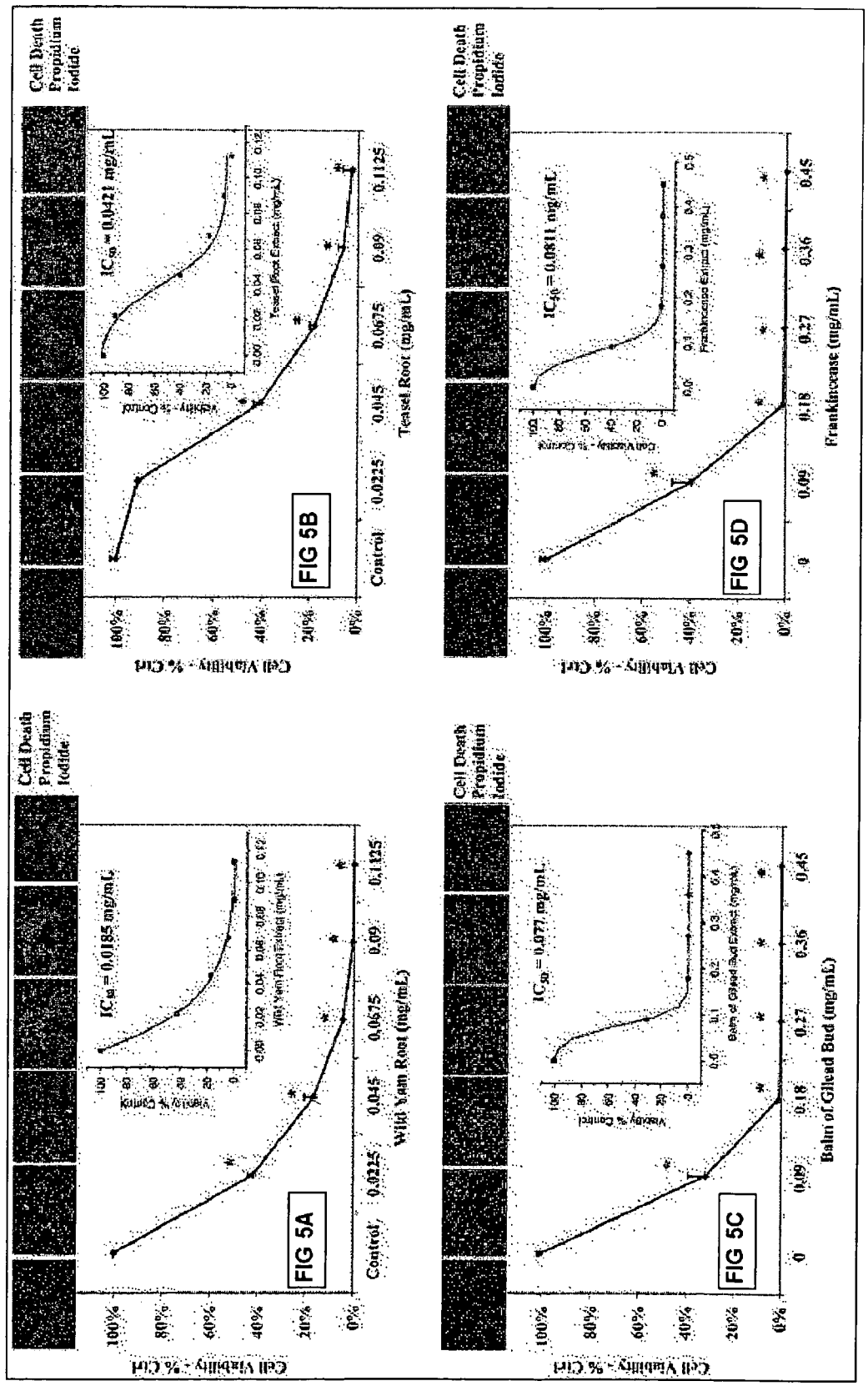

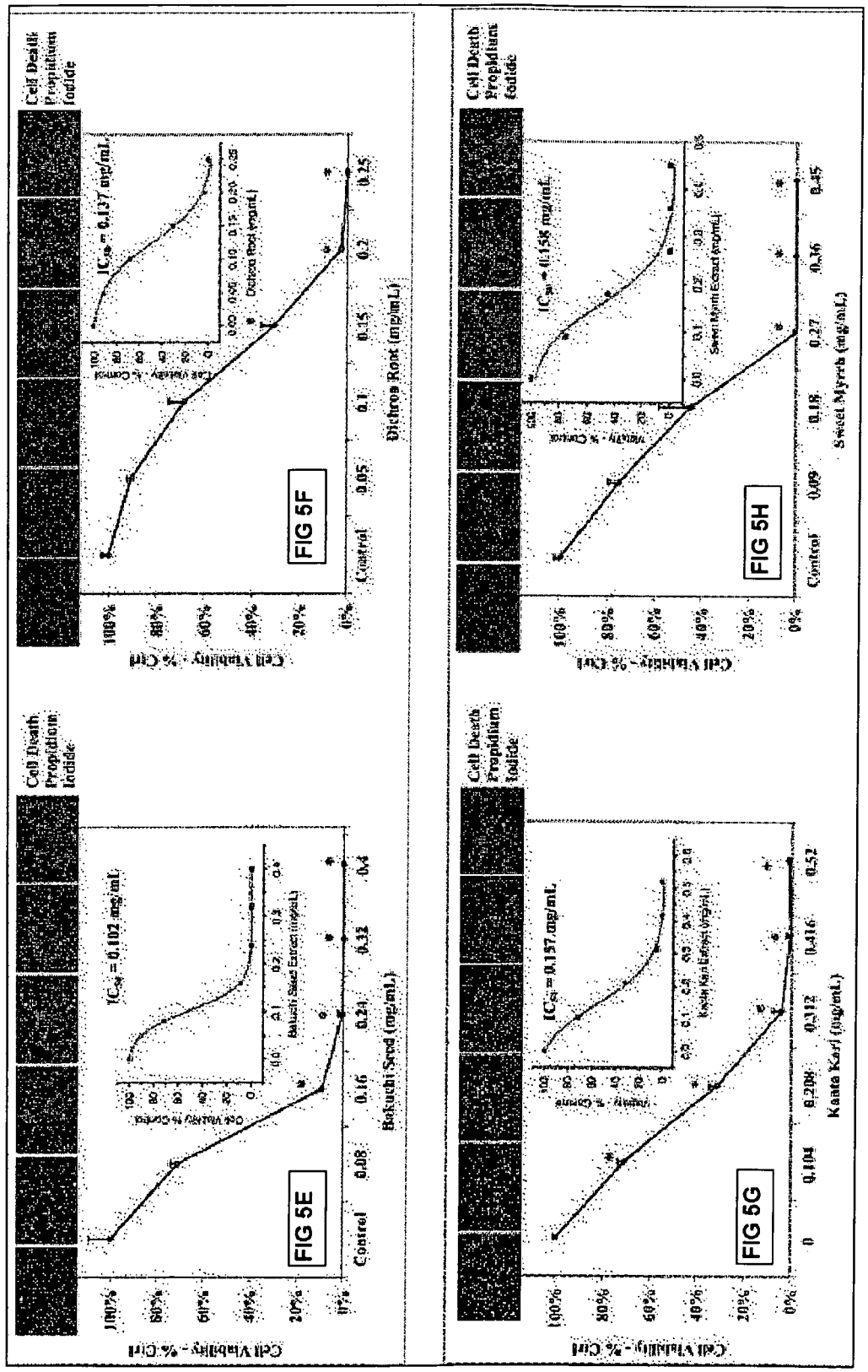

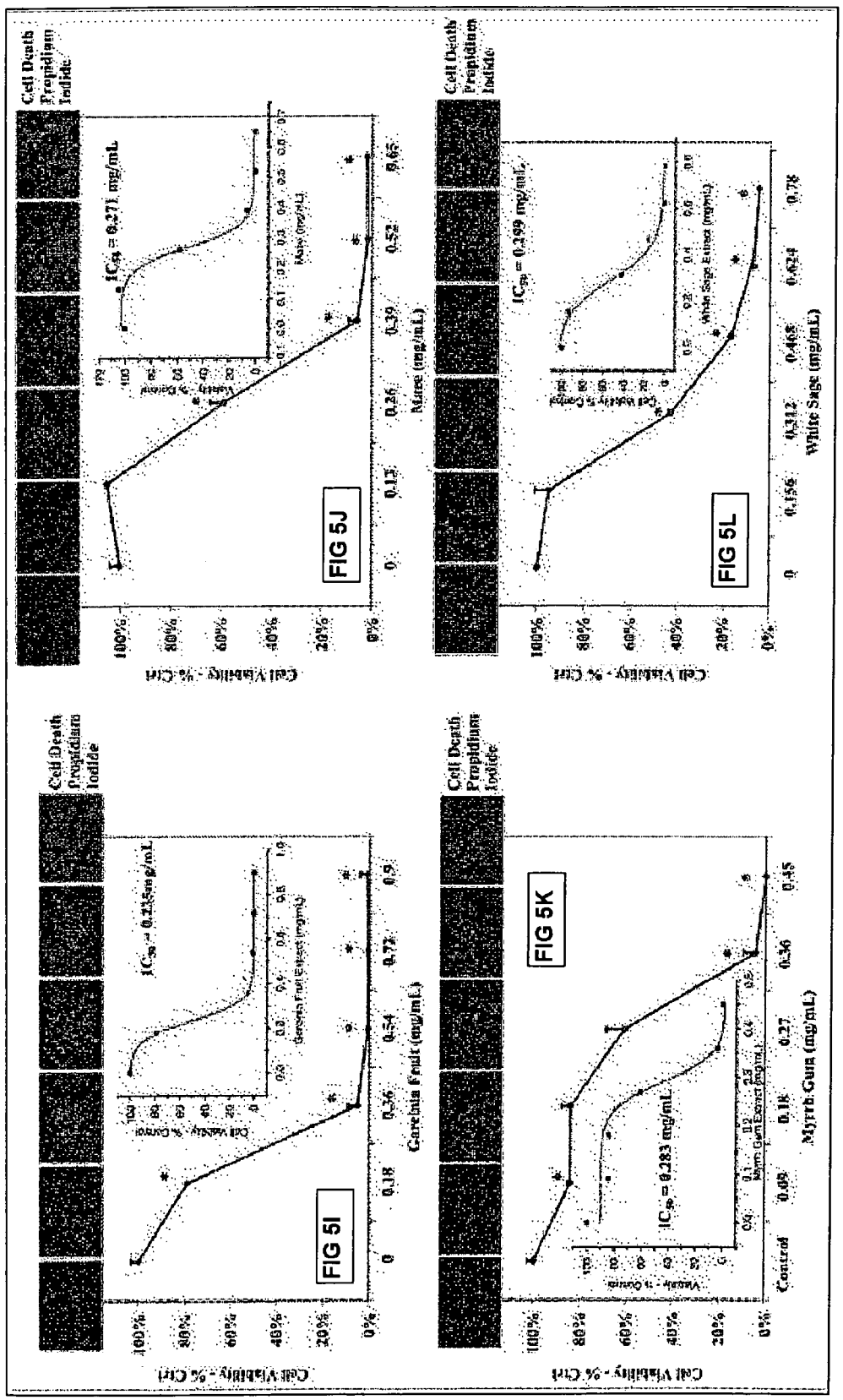

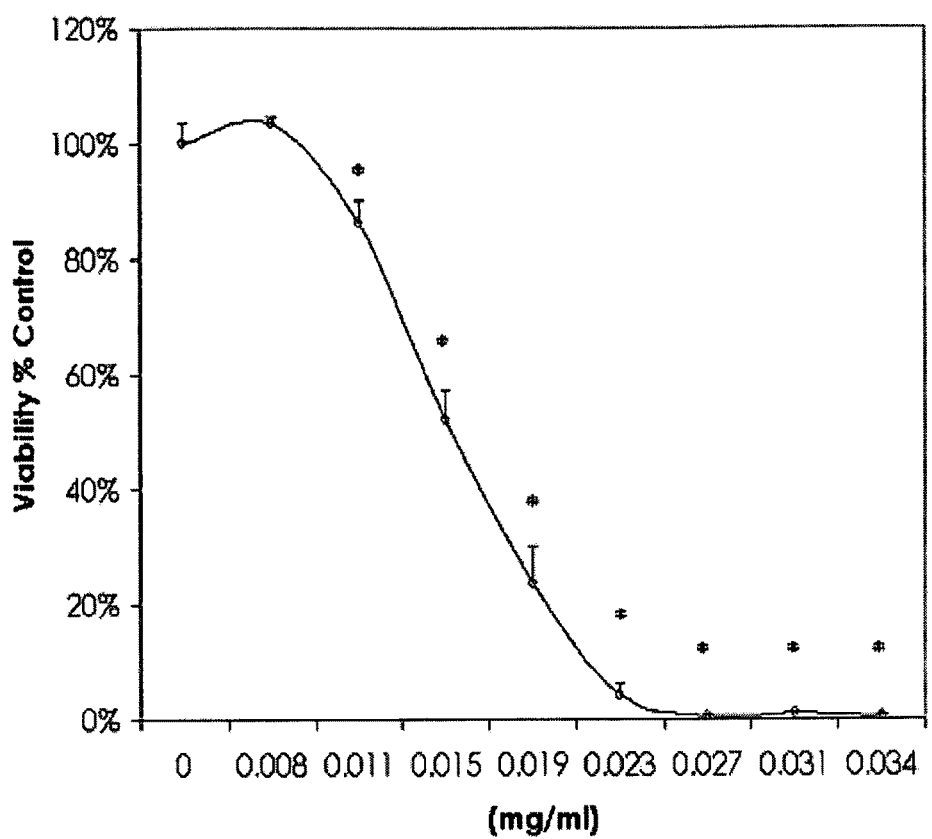
Figure 6  Tumoricidal Potency of *Lithospermum erythrorhizon* Extract in Malignant Neuroblastoma @ 24 Hours

HERBAL COMPOSITION AND METHOD OF USE FOR THE TREATMENT OF CANCER

CROSS-REFERENCE TO RELATED APPLICATIONS

This application is a continuation in part of application Ser. No. 11/711,883 filed on Feb. 27, 2007 which is a continuation in part of application Ser. No. 11/233,279 filed on Sep. 21, 2005, now abandoned, which is a continuation in part of application Ser. No. 10/909,590 filed on Aug. 2, 2004, now abandoned, which claims the benefit under 35 USC 119 (e), of previous provisional application(s) No. 60/491841 filed on Aug. 2, 2003 and No. 60/540525 filed on Jan. 30, 2004, all of which are herein incorporated by reference.

STATEMENT REGARDING FEDERALLY SPONSORED RESEARCH AND DEVELOPMENT

The U.S. government has certain rights to this invention as federal support was provided for by NIH Grant NCRR 03020.

FIELD OF THE INVENTION

The enclosed describes a nutraceutical composition and method for treatment and/or prevention of human and animal cancers. The invention therefore, relates to the fields of nutrition, herbal medicine, pharmacology, oncology, medicine, medicinal chemistry and biochemistry.

DESCRIPTION OF THE RELATED ART

Chemotherapy agents often render concurrent toxic effects to the body and the cancer, which ultimately contribute to a narrow therapeutic index. The objective of this invention to establish a nutritional/herbal formulation for use in cancer prevention or treatment to widen the gap by using natural non-toxic substances target the tumor without harm to the host. The formulation is in part based on our in vivo and in vitro findings from ranking a large number of supplements/herbs which are currently sold in the US, China and India for tumoricidal properties. In addition, we investigated the mechanism of action by which these agents exert their effects. In summary, this is a broad based herbal/vitamin nutraceutical supplement that may serve useful as a safe and effective complementary and alternative medicine (CAM) to augment traditional cancer treatment for humans and animals.

The use of CAM's generally serve to augment the health and function of the spirit, mind and body to the inclusion of herbal and natural supplemental use. A large number of individuals including approximately 36% of adult Americans use CAM on a regular basis to the aggregate cost of $36-$47 billion dollars annually (Advance Data from vital and health statistics, May 27, 2004 CDC). A growing inclination toward CAM use by consumers world wide is occurring due to a) the soaring rise in the cost of heath care b) greater access to information via the world-wide web c) failure of prescription drugs to effectively treat diseases to prevent morbidity or mortality and d) a greater global conscience toward the importance of holistic medicine. With regard to cancer, it is estimated that up to 91% of patients seek some form of CAM, with greatest percentages observed amongst breast, pediatric, prostate, head and neck cancer patients (Molassiotis et al., Complement Ther Med. 2005; 13(4):251-7; Kumar et al., Cancer Control. 2005; 12(3):149-57; Yates et al., Support Care Cancer. 2005; 13(10):806-11, Kim et al., Korean J Intern Med. 2004; 19(4):250-6; Buettner et al., Breast Cancer Res Treat. 2006; 100(2):219-27; Mansky et al., Cancer J. 2006; 12(5):425-31; Nahleh and Tabbara Palliat Support Care. 2003; 1(3):267-73).

There are several problems that arise with use of CAM to treat cancer. First, patients are not likely to communicate practices to primary care physicians (Roberts et al., J Psychosoc Oncol. 2005; 23(4):35-60), where self administration is based on the perception that these agents can boost the immune system (McEachrane-Gross et al., BMC Complement Ahern Med. 2006; 6:34), increase survival rate, improve quality of life, reduce pain/chemotherapy side effects (Nahleh and Tabbara, Palliat Support Care. 2003; 1(3):267-73: Hana et al., Isr Med Assoc J. 2005; 7(4):243-7), ameliorate depression and promote a greater sense of control over the disease (Singh et al., Integr Cancer Ther. 2005; 4(2):187-94; Pud et al., Eur J Oncol Nurs. 2005; 9(2):124-30). Moreover, the choice of CAM's used are often initiated by word of mouth advice from friends, family members and associates even though much of the information has not been scrutinized scientifically (Molassiotis et al., Complement Ther Med. 2005; 13(4):251-7; Lowenthal Med J Aust. 2005; 183(11-12): 576-9).

According to prior art, some of the most popular cancer-specific CAMs are known to include dietary supplements and herbs (Swarup et al., Am J Clin Oncol. 2006; 29(5):468-73; Molassiotis et al., Int J Gynecol Cancer. 2006; 16 Suppl 1:219-24) of which include stinging nettle, lime, rosehips, bee pollen, mulberry molasses, ginger, bee milk, spiders web, garlic, green tea, tomatoes, soy products (Boon and Wong, Expert Opin Pharmacother. 2004; 5(12):2485-501; Algier et al., Eur J Oncol Nurs. 2005; 9(2):138-46; Karadeniz et al., Pediatr Blood Cancer. 2006 August 9), mistletoe, ginseng (Melnick, J Pediatr Hematol Oncol. 2006; 28(4):221-30), barberry, bilberry, cayenne, chamomile, don quai, feverfew, ginko, green tea, kava, silymarin, licorice, meadowsweet, motherwort, senna leaf, sheperds purse, St. johns wort, tumeric, valerian, mushrooms (Advance Data from vital and health statistics, May 27, 2004; Kumar et al Cancer Control. 2005; 12(3):149-57; Melnick. J Pediatr Hematol Oncol. 2006; 28(4):221-30; Gerson-Cwilich et al., Clin Transl Oncol. 2006; 8(3):200-7; Dy et al., J Clin Oncol. 2004; 22(23):4810-5; Hu et al., Drugs. 2005; 65(9):1239-82) shark cartilage, essiac, vitamins C and E (Armstrong et al., J Pain Symptom Manage. 2006; 32(2):148-54), calcium, selenium, coenzyme $Q_{10}$, zinc, potassium and saw palmetto (Chan et al., Urology. 2005; 66(6):1223-8). And, while many individuals report the positive effects realized by CAMs, there are also studies showing lack of therapeutic value in clinical trials (Loprinzi et al., Cancer. 2005 1; 104(1):176-82; Tas et al., Acta Oncol. 2005; 44(2):161-7).

The nutraceutical as described in this embodiment is novel in terms of constituents and design. In brief, we conducted a large scale screening of over 700 commonly sold nutritional supplements for relative tumoricidal properties in vitro. And, we proposed a rationale based on metabolic targeting to minimize chances of tumor cell survival. In brief, the formulation consists of nutraceutical compounds that should antagonize 1) anaerobic glucose metabolism by inhibiting lactic acid dehydrogenase LDH (LDH—) 2) favor oxidative mitochondrial function (OXPHOS+) by optimizing aerobic respiration 3) alter the body's pH toward alkaline and 4) exert anti-proliferative/pro-apoptotic properties. Many agents that looked promising at the onset, were eliminated from the formulation design due to lack of safety data, reported contraindications in either experimental research, historical knowledge, advisories by the American botanical counsel or review of the German Herbal Regulatory Commission E monographs. The proposed formulation is speculated to be safe for human consumption without side effects.

1. Oxidative Phosphorylation Component (OXPHOS+). The pathogenesis of cancer involves an obvious abnormality of glucose metabolism, one significantly different from typical oxidative metabolic processes of eukaryotic cells. Original studies by Otto Warburg reveal robust glycolytic activity in cancer cells even in the presence of oxygen ("$O_2$"). Many studies have since then corroborated these findings where general tumor tissue exhibits a) rapid consumption of glucose b) robust glycolytic activity c) rapid cell proliferation d) production and accumulation of lactic acid and e) a low extracellular pH with depleted glucose levels circumscribing the perimeter of the tumor. Our baseline findings are consistent with these observations (Mazzio et al., Brain Res. 2004 Apr. 9; 1004(1-2):29-44), where enormous lactate is produced during routine metabolism, substantiating that energy (ATP) is produced primarily through anaerobic substrate level phosphorylation in the cytoplasm even in the presence of functional mitochondria. The data from our research indicate that cancer cells a) survive without $O_2$ b) prefer $CO_2$ and c) that changes in $O_2/CO_2$ are intricately involved with the way in which cancer cells metabolize glucose which subsequently control cell death or cell viability/proliferation. In contrast to the host, an inverse relationship between mitochondrial function in cancer cells exists, where blocking mitochondrial respiratory function (e.g. mitochondrial monocarboxylic pyruvate transport blocker, toxins such as 1-methyl-4-phenylpyridinium (MPP+), rotenone, absence of $O_2$/high concentration of $CO_2$) are all conditions which prompt a robust potentiation of glucose metabolism through glycolysis (indicative of metabolic potentiation), while having no toxic effects other than depletion of glucose supply in a glucose-limited environment (Mazzio and Soliman, Biochem Pharmacol. 67:1167-84, 2004). In contrast, optimizing mitochondrial respiration in cancer cells could hamper anaerobic glucose utility. The findings suggest that glucose metabolism in cancer is in direct opposition to the host, which favors aerobic oxidation of glucose, where enhanced mitochondrial function is beneficial, mitochondrial toxins are poisonous and a high concentration of $CO_2$ leads to suffocation through the halt of mitochondrial energy.

Congruent with these observations, $O_2$ deprivation or tissue hypoxia exacerbates the growth of cancer and resistance to chemotherapy (Brizel et al., Int. J. Radiat. Oncol. Biol. Phys., 51:349-53, 2001; Brizel et al, Int. J. Radiat. Oncol. Biol. Phys., 38:285-290, 1997; Alagoz et al., Cancer 75:2313-22, 1995) and propels glycolysis (Nielsen et al., Cancer Res. 61:5318-25, 2001). Likewise, high levels of $O_2$ induced by use of carbogen (95% $O_2$/5% $CO_2$) are notably helpful in augmenting radiotherapeutic response to transplanted rat GH3 prolactinomas (Robinson et al., Br J. Cancer, 82: 2007-14, 2000). Similarly, use of hyperbaric $O_2$ arrests the growth of tumors resistant to chemotherapy and potentiates the effects of cisplatin (Alagoz et al., Cancer 75:2313-22, 1995). These studies all support that cancer is a facultative anaerobe, having adverse reaction to heightened levels of $O_2$. Further analysis in our lab has revealed two possible mechanisms for the toxicity of oxygen on cancer cells. The first being heightened mitochondrial respiration (where oxygen is a substrate for mitochondrial complex IV) second to the measurable rise in alkalinity which occurs in the presence of oxygen. Both $O_2$ and $CO_2$ are critical in regulating oxidative/non oxidative glucose metabolism and acid-base homeostasis where $CO_2$ in aqueous solution to which it is exposed produces carbonic acid, which decreases the pH thereby providing accommodating conditions for cancer cells to thrive. In contrast, high levels of oxygen create a rise in alkalinity to which cells are extremely vulnerable, where even a slight rise above neutral [pH=7.4+0.5] was found to initiate cancer cell death (data not shown). Further noted, if the rise in alkalinity induced by oxygen is neutralized with a strong acid, negative consequences of cell death are not realized. These findings indicate the importance of an alkaline pH in the initiation of cancer cell death.

While this invention includes several targeted mechanisms by which to optimize the aerobic/anaerobic metabolic ratio in host and cancer, first addressed is potentiation of aerobic mitochondrial function. The data from our research show that heightening the function of the mitochondria primarily through augmenting the $V_{max}$ and reduction of $K_m$ of mitochondrial complex's I and IV can be achieved by vitamin $B_2$ (riboflavin: 7,8-dimethyl-10-ribityl-isoalloxazine), its derivatives flavin mononucleotide (FMN) and flavin adenine dinucleotide (FAD). Flavins yield robust enhancement of $O_2$ utilization through cytochrome oxidase in cancer cells creating impedance on the ability of cancer cells to use glucose to produce ATP through substrate level phosphorylation (Mazzio and Soliman, Biochem Pharmacol. 67:1167-84, 2004). Previous literature regarding riboflavin in the treatment of cancer remains ambiguous and unclear. Earlier studies suggest that riboflavin antagonists (eg. diethyl riboflavin) will exert anti-tumor effects, where riboflavin supplementation could accelerate tumor growth and metastasis (Nutr Rev. 1974 October; 32(10):308-10; Shapiro et al., Cancer Res. 1956 August; 16(7):575-80). However, recent studies show that riboflavin is protective against carcinogenesis induced by azo compounds (Rivlin, Cancer Res. 1973 September; 33(9): 1977-86) and a deficiency, pre-empts cervical dysplasia and cancer, an effect reversed by high intake of riboflavin in both animals and humans (Thurnham et al., Nutr Cancer. 1985; 7(3):131-43; Chen et al., Nutr Cancer. 2002; 42(1):33-40; Powers H J, Am J Clin Nutr. 2003 June; 77(6):1352-60; Petridou, Nutr Cancer. 2002; 44(1):16-22; La Vecchia et al., Int J Cancer. 1997 Nov. 14; 73(4):525-30; Key, Proc Nutr Soc. 1994 November; 53(3):605-14.).

Similarly, prior art in terms of patent publications suggest riboflavin may be beneficial in reducing the toxic effects of chemotherapy (WO03/045372, 06-05-2003, Burzynski and Kammerer), its use in combination with lumichrome derivative could suppress tumor growth (JP6279445, 10-04-1994, TSuzaki), and as an enrichment with vitamin E, chinese medicines scorpion, Fructus lycii, Radix glycyrrhizae, Fructus zizyphi jujubae, Rhizoma smilacis glabrae, and Flos chrysanthemi and crop liqour could treat cancer and senility (CN1081467, 02-02-1994, Belin). Riboflavin has also been described as a component to anti-cancer foods with nicotinic acid and amino acids (JP58170463, 10-07-1983, Asoujima). Riboflavin also appears in large range of patent publications for use in a wide variety maladies including toxic shock (WO 97/36594, 03-28-1997, Araki et al.,), infections, septic shock (WO 02/074313, 3-19-2003, Araki et al.,), headache (WO 02/11731,07-20-2001, Valletta and Banchetti), high cholesterol (WO 02/34261, 10-21-2001, Ohsawa et al.,) weight loss (WO 02/060278, 6-13-2001, Gaetani and Cavattoni), acne (U.S. Pat. No. 6,558,656,06-06-2003, Mann), diseases of genital and mucous membranes (U.S. Pat. No. 6,020,333,02-01-2000, Berque), viral infections (CA 2174552, 04-27-1995, Washington et al.,), macular degeneration (U.S. Pat. No. 5,075,116,12-24-1991, LaHaye), immune disorders (WO 03/084545, 04-09-2003, Araki et al.,), hemorrhoids (CA 1147656, 06-07-1983, Breskman), and as a part of nutritional supplement formulations as one of the B-complex vitamins (U.S. Pat. No. 6,245,360,06-12-2001, Markowitz).

2. Lactic Acid Dehydrogenase Inhibition: LDH (−) Second to optimizing mitochondria function, the formula also contains a nutraceutical compound that can inhibit lactic acid dehydrogenase (LDH-V). LDH plays a critical role in the progression of cancer (Shim et al., Proc Natl Acad Sci USA. 94:6658-63. 1997; Sun et al., Zhonghua Zhong Liu Za Zhi 13:433-5, 1992) A downregulation of LDH in BGC-823 gastric carcinoma induces tumoricidal effects (Yang et. al, Zhonghua Zhong Liu Za Zhi 18:10-2, 1996) and the remission of cancer and survival rates in humans undergoing chemotherapy to platinum drugs corresponds to a diagnostic reduction in serum LDH (Velasquez et al., Blood 71:117-22, 1998). The rise in LDH plays a critical role in directing aggressive malignancies (Walenta and Mueller-Klieser. Semin Radiat Oncol 2004; 14:267-74), because its enzyme function is required to generate NAD+ as an enzymatic product and cofactor for glyceraldehyde-3-phosphate dehydrogenase to propel ATP production through phosphoglycerate/pyruvate kinase (anaerobic metabolism). The LDH inhibiting agent in the nutraceutical formulation should specifically target the enzyme, where the remainder of the glycolytic pathway to the production of pyruvate remains unaffected. This is critical given that the glycolytic pathway converts 1 mole of glucose to 2 moles of pyruvate, which then can diverge to fuel either anaerobic metabolism through LDH or it is transported to the mitochondria where it is converted to acetyl-CoA by pyruvate dehydrogenase to sustain aerobic (oxidative) metabolism in the host. The latter metabolic pathway is required by the host, and leads to the ultimate generation of reducing equivalents (NADH2/FADH2) by clockwise tricarboxylic acid cycle activity, for entry into the electron transport chain to produce ATP (Armstrong and Frank, Biochemistry-Second Edition, New York, Oxford University Press Inc., 1983).

Our findings show that LDH is required by cancer cells, where the host requires mitochondrial oxidative function. We also found that many anti-cancer flavonoids commonly consumed and sold over the counter also inhibit the activity of LDH (LDH-5 ($M_4$)) (not yet published), an enzyme most resembling that inherent to human cancer (Koukourakis et al., Br J Cancer. 2003; 89:877-85; Augoff and Grabowski. Pol Merkuriusz Lek 2004; 17:644-7; Nagai et al., Int J Cancer. 198815; 10-6; Evans et al., Biol. Chem. 1985; 260:306-14). Yet, use of these LDH (−) do not have side effects and this mechanism has not yet been considered as a means by which these compounds exert known anti-cancer effects (Rosenberg et al., J Chromatogr B Analyt Technol Biomed Life Sci. 777: 219-32, 2002; Stoner and Mukhtar, J Cell Biochem Suppl. 22:169-80, 1995). From a screening of potential LDH (−) emerged rationale for the use of inhibitor 2',3,4'5,7-pentahydroxyflavone (herein also referred to as "morin"). Supportive research studies have corroborated efficacy of morin against proliferation of carcinoma cells which is believed due to inactivation of the cell cycle kinase, activation of the mitogen/stress pathway kinases (Brown J, O'Prey J, Harrison P R., Carcinogenesis. 2003 February; 24(2):171-7) and inhibition of topoisomerase I (Boege F, Straub T, Kehr A, Boesenberg C, Christiansen K, Andersen A, Jakob F, Kohrle J., J Biol. Chem. 1996 Jan. 26; 271(4):2262-70). Pentaallyl ethers of morin are also known to be anti-tumor agents, which inhibit p-glycoprotein ATP efflux of chemotherapy drugs in drug resistant cells (Ikegawa et al., Cancer Letters: 2002; 177: 89-93). Use of morin has also been described in combination with other flavonoids in patent publications for antimicrobial agents (JP2004250406. 09-09-2004, Danno Genichi and Arima Hidetoshi), treatment of diaper rash (JP2004091338, 03-25-2004, Tamura Kokichi), an anti-tumor agent (JP2001055330, 02-27-2001, Tanaka Takuji), substances that control plant fertility (U.S. Pat. No. 5,733,759, 03-31-1998, Taylor Loverine and Mo Yinyuan) and treatment of chlamydial infection (CA 2419716, 02-21-2002, Vuorela, Pia et al.,) or radiation dermatitis (U.S. Pat. No. 6,753,325,06-22-2004, Rosenbloom). While we morin could be the LDH inhibitor of choice, we also propose a host of alternative LDH inhibitors (herbal extracts) based on data generated on LDH enzyme kinetic profiles in our lab evident for: epigallocatechin gallate, quercetin, citric acid, rosemary (*Rosmarinus officinalis*), black walnut (*Juglans nigra*), clove (*Syzygium aromaticum*), nutmeg (*Myristica fragans*), licorice root (*Glycyrrhiza glabra*), coriander (*Coriandrum sativum*), cinnamon (*Cinnamomum cassia*), ginger root (*Zingiber officinale*), myrrh gum (*Commiphora molmol*) and green tea (*Camellia sinensis*).

3. Unknown inhibitory component (AIC(−)). The third metabolic pathway that we are currently exploring is as of yet is not clear, but appears to control anaerobic metabolism via central cytosolic carboxylation reactions. The use of (2,3-dimethoxy-5-methyl-1,4-benzoquinone (herein also termed "DMBQ") (quinoid base)) is no doubt lethal to cancer cells, and could be targeting a number of enzyme systems such as acetate-coA ligase, malate synthase, isocitrate lyase, aconitase, phosphoenolpyruvate carboxylase/carboxykinase, glycolate oxidase, phosphoglycolate phosphatase, glycolaldehyde dehydrogenase, pyruvate carboxylase, citrate lyase, ferridoxin oxidoreductase, fructose 1,6-bisphosphatase, 2,3-diphosphoglycerate mutase, propionyl CoA carboxylase and/or malic enzyme.

There is very little known about the potential uses for DMBQ or the short chain ubiquinones. Of the few published items include a patent that describes the use of CoQ0 in an oral hygiene formulation owned by SmithKline (WO03037284, 05-08-2003, Hynes) and use of coenzyme Q2, Q4, Q6 in a method for treating or preventing mitochondrial dysfunction associated with Friedreich Ataxia, hypertrophic cardiomyopathy, Hallervorden-Spatz disease and sideroblastic anemia (U.S. Pat. No. 6,133,322, 10-17-2000, Rustin and Roetig). Coenzyme Q2 has been used as a component in a formulated treatment for dementia (JP4112823, 04-14-1992, Imagawa) and Q9 has been described in combination with $CoQ_{10}$ for poultry feed formulations (EP0913095, 05-06-1999, Aoyama and Sugimoto). While there are no published research studies investigating use of DMBQ against cancer, a few studies have defined its protection against lipid peroxidative in kidney, liver, heart, lung and spleen in animal models of oxidative injury and without side effects at high administrative concentration (Knudsen et al., Free Radic Biol Med. 1996; 20(2):165-73; Chen and Tappel, Free Radic Biol Med. 1995 May; 18(5):949-53). On the other hand, structurally related derivatives of CoQ (e.g chloroquinones and alkylmercapto-1,4-benzoquinones) (Porter et al., Bioorganic Chemistry 1978: 7:333-350; Folkers et al., Res Comm Chem Path Pharm 1978: 19(3) 485-490; Wikholm et al., Journal of Med Chem 1974:17:893-896) and a range of structurally similar compounds (e.g. 2,5-diaziridinyl-3,6-bis (carboethoxyamino)-1,4 benzoquionone (U.S. Pat. No. 4,233,215, 11-11-1990, Driscoll et al.,) and 6-methoxy-10-cis-heptadecene-1,4-benzoquinone (CN 1362061, 08-07-2002, Dehua et al.,) have been described as anti-tumor agents.

While there are meager uses defined for DMBQ, there is abundant information regarding $CoQ_{10}$ which plays a central role in mitochondrial enzymes that carry out oxidation-reduction reactions involved with aerobic ATP production. $CoQ_{10}$ is not a critical component of this invention, as our studies show that while $CoQ_{10}$ can increase the $V_{max}$ of mitochondrial complex II activity in cancer cells (Mazzio and Soliman, Biochem Pharmacol. 67:1167-84, 2004), this did not control the rate of mitochondrial respiration or $O_2$ utilization through complex IV. And, $CoQ_{10}$ was not as lethal as expected. Likewise, results of $CoQ_{10}$ against cancer have been contradictory. For example, several reports demonstrate a positive inverse correlation where low physiological $Q_{10}$ concentrations are associated with greater risk for cancer (Palan P R et al., Eur J Cancer Prev. 2003 August; 12(4):321-6; Portakal et al., Clin Biochem. 2000 June; 33(4):279-84; Jolliet P et al., Int J Clin Pharmacol Ther. 1998 September; 36(9):506-9) and its administration induces tumoricial effects (Gorelick C et al., Am J Obstet. Gynecol. 2004 May; 190(5):1432-4), blocks the growth of cancer (Lockwood K et al., Biochem Biophys Res Commun. 1995 Jul. 6; 212(1):172-7; Lockwood et al., Biochem Biophys Res Commun; 1994 Mar. 30; 199(3)1504-1508; Folkers et al., Biochem Biophys Res Commun 1993 Apr. 15; 192(1) 241-245) and reduces side effects of chemotherapy (Roffe L et al., J Clin Oncol. 2004 Nov. 1; 22(21): 4418-24; Perumal S S et al., Chem Biol Interact. 2005 Feb. 28; 152(1):49-58). However, the positive results are not always reported (Roffe et al., Journal of Clin Oncology 2004; 22(21) 4418-4424; Prieme H et al., Am J Clin Nutr. 1997 February; 65(2):503-7; Hodges et al., Biofactors 1999; 9(2-4):365-70; Lesperance et al., Breast Cancer Res Treat. 2002 November; 76(2):137-43) and the use of HMG-CoA inhibitors which lower endogenous production of cholesterol and $CoQ_{10}$ do not appear to be a pre-determinant to cancer (Sacks et al., Reply letters to the editor JACC 1999 33 (3): 897-898). Other reported uses of $CoQ_{10}$ include to ameliorate end-stage heart failure (Berman M et al., Clin Cardiol. 2004 May; 27(5):295-9; Erman A, Ben-Gal T, Dvir D, Georghiou G P, Stamler A, Vered Y, Vidne B A, Aravot D), chronic heart failure (Mortensen S A Biofactors. 2003; 18(1-4):79-89), hypertension, hyperlipidemia, coronary artery disease (Sarter B. J Cardiovasc Nurs. 2002 Jut; 16(4):9-20), heart complications associated with use of statin drugs (Langsjoen P H and Langsjoen A M. Biofactors. 2003; 18(1-4):101-11; Chapidze G et al., Georgian Med. News. 2005 January; (1):20-5), hypertriglyceridemia (Cicero A F et al., Biofactors. 2005; 23(1):7-14), chronic fatigue (Bentler S E et al., J Clin Psychiatry. 2005 May; 66(5):625-32), alzheimer's disease, parkinson's disease (Ono K et al., Biochem Biophys Res Commun. 2005 Apr. 29; 330(1):111-6; Beal M F. J Bioenerg Biomembr. 2004 August; 36(4):381-6), oxidative neurodegenerative injury (Somayajulu M et al., Neurobiol Dis. 2005 April; 18(3):618-27), migraine headaches (Sandor P S et al., Neurology. 2005 Feb. 22; 64(4):713-5), age-related loss of cognitive function (McDonald S R et al., Free Radic Biol Med. 2005 Mar. 15; 38(6):729-36), muscle and cardiomyopathies (Lalani S R et al., Arch Neurol. 2005 February; 62(2): 317-20), hyperthyroidism (Menke T et al., Horm Res. 2004; 61(4):153-8), preeclampsia (Teran E et al., *Free Radic Biol Med.* 2003 Dec. 1; 35(11):1453-6) and cerebellar ataxia (Lamperti C et al., Neurology. 2003 Apr. 8; 60(7):1206-8). In terms of patent literature, $CoQ_{10}$ is known to treat cancer (WO 02/078727, 02-24-2004, Van De Wiel), endothelial dysfunction (CN1471390, 01-28-2004, Watts and Playford), skin (US2005036976, 02-07-2005, Rubin and Patel), cardiovascular and weight gain (US2004028668, 02-12-2004, Gaetani), arteriosclerosis (US2004248992, 12-09-2004, Fujii et al.,) periodontosis (U.S. Pat. No. 6,814,958,11-9-2004, Sekimoto), post-surgical opthalmologic pathologies (U.S. Pat. No. 6,787,572,09-07-2004, Brancato, et al.), neurodegenerative disease, memory loss (U.S. Pat. No. 6,733,797,05-11-2004, Summers), mitochondrial disorders (CA2285490, 04-07-2001, Sole and Jeejeebhoy), diabetes (CA2476906, 09-25-2003, Fujii et al,) and as a part of formulations that comprise antioxidants (CA2457762, 04-10-2003, De Simone), hair or scalp treatment (CA 2444282, 12-19-2002, Kawabe), sunscreen (CH693624, 11-28-2003, Gecomwert) and food supplements (U.S. Pat. No. 6,642,277, 11-04-2003, Howard et al.,).

4. Alkalizing Agent (Alkaline+); The base formulation incorporates an alkalizing regime with use of substances including *aloe vera, chlorella*, wheat grass, apple cider vinegar, burdock root, kudzu root, alfalfa, barley grass, spirulina, parsley leaf and calcium, magnesium, potassium or bicarbonate salts.

5. Antiproliferative Herbs (Proliferation (−)); include Speranskia Herb (*Speranskia tuberculata*) or Goldenseal (*Hydrastis Canadensis*), and the most potent tumoricidal herbal supplements include: wild yam (*Dioscorea Villosa*), beth root (*Trillium Pendulum* Root), Teasel Root (*Dipsacus asper*), Balm of Gilead Bud (*Populus balsamifera*), Frankincense (*Boswellia carteri*), Bakuchi Seed (*Cyamopsis psoralioides*), Dichroa Root (*Dichroa febrifuga*) of Kanta Kari (*Solanum xanthocarpum*), Bushy Knotweed Rhizome (*Polygonum Cuspidatum*) gromwell root (*Lithospermum erythrorhizon* root), galbanum (*Ferula galbaniflua*) garcinia Fruit (*Garcinia cambogia*), white sage (*Salvia apiana*) or constituent chemicals gambogic acid, shikonin, diosmin and boswellic acid.

The prior art describing the most potent tumoricidal herbs is as follows. There are little to no reports indicating use of wild yam or beth root for cancer, however diosgenin (a constituent of wild yam) when used alone is known to exert antiproliferative pro-apoptotic effects in tumor cells, both arresting G2/M, and downregulating NF-kappa B, Akt, cyclin D, c-myc, leading to PARP cleavage and DNA fragmentation (Shishodia and Aggarwal, Oncogene. 2006; 25(10):1463-73; Leger et al., Int J Oncol. 2006; 28(1):201-7; Liagre et al., Int J Mol. Med. 2005; 16(6):1095-101; Li et al., Nephron Exp Nephrol. 2005; 101(4):e111-8, Liu et al., Cancer Chemother Pharmacol. 2005; 55(1):79-90). The use of wild yam dates back centuries and to date the American Herbal Products Association—Botanical Safety Handbook (AHPA-BSH) has defined this herb as a Class-1 herb (safest herb category), further defined as "herbs which can be safely consumed when used appropriately". However, experimental studies show oral administration of wild yam root extract in animals to be safe at 0.5 mg/kg, but higher concentrations (2.0 g/kg) can espouse serious adverse effects such as hypoactivity, piloerection, dyspnea and death (Int J Toxicol. 2004; 23 Suppl 2:49-54.

Teasel Root (*Dipsacus asper*) is commonly used to treat lime disease, fibromyalgia, also serving as a generic cleanser for the liver, kidney, digestive and circulatory system. Our data show that extract of teasel root shows considerable promise as an anti-cancer herb because of its lethal effects at very low concentration, combined with its use not being associated with reported or known side effects. There is no research regarding the use of this herb as an anti-cancer agent, however a recent study suggested potential in the treatment of Alzheimer's disease (Zhang et al., Life Sci. 2003; 73(19):2443-54) and other diseases involving oxidative stress (Kim et al., Phytother Res. 2005; 19(3):243-5). Teasel root is commonly sold with a suggested product dose of 6-21 g/day which is quite high for human consumption. Furthermore, because teasel root is quite safe at high doses, categorized as a AHPA-BSH Class 1 herb, this herb could readily be a central component to a holistic anti-cancer formulation (McGuffin, American Herbal Products Association's Botanical Safety Handbook CRC Pr Inc., 1997).

Like wild yam and teasel root, there is also a complete absence of scientific research literature regarding potential application of Balm of Gilead Bud (*Populus balsamifera*) and its anti-cancer effects. Historical use of this herb, however, extends back to the Native Americans for treatment of urinary infections, wounds, colds, arthritis, pains, coughs and as an effective insect repellent. Consumer applications for Balm of Gilead bud have been approved as "safe" by the German Commission E for topical applications only such as for treatment of skin disease, external hemorrhoids, frostbite and sunburn (Bundesinstitut fur Arzneimittel and Medizinprodukte. The Complete German Commission E Monographs: Therapeutic Guide to Herbal Medicines Lippincott Williams & Wilkins; 1998. Herbalgram online database). However, alcohol extracts of balm of gilead bud are marketed and sold by a number of nutritional manufacturers with instructions for internal for up to 2 mls/day, with no known reported side effects. The German Commission E reports state its use has no known drug interactions, no restrictions applicable during pregnancy or lactation, with precaution for use in individuals who are allergic to propolis or aspirin (salicylic acid). This is a AHPA-BSH Class 1 herb indicating it is relatively safe, however allergic reaction to aspirin occur in approximately 1% of the population, with greater likelihood in individuals who suffer from other allergic reactions such as hives, asthma and sinus infections (McGuffin, American Herbal Products Association's Botanical Safety Handbook CRC Pr Inc., 1997). In these individuals, serious side effects can include Reye's syndrome, severe liver inflammation, brain damage and death. This herb could readily be incorporated into the formulation, but must be omitted for application toward any individual who experiences allergic reaction to aspirin.

The reported use of Frankincense (*Boswellia carteri*) dates back to 3000 BC where it was exported from Arabia to Egypt and the Roman Empire for use primarily as incense, until the year 200 A.D. where export went up to 3000 tons/annually and utility expanded to medicinal purposes including treatment of gout, ulcers, oral health and its use in manufactured plasters (Hillson, J R Soc Med. 1988; 81(9):542-3). The potential for frankincense as an anti-cancer agent in this study corroborates the first documented science literature which appeared in 1991, reporting frankincense effective to inhibit topoisomerase II in mouse leukemia L1210 cells similar to etoposide and aclarubicin (Wang et al., Zhongguo Yao Li Xue Bao 1991; 12(2):108-14). The use of frankincense in the treatment of cancer shows considerable promise as boswellic acid pentacyclic triterpenes derived from the gum resin are known to be more potent than camptothecin, amsacrine or etoposide in inhibiting human topoisomerases I and II alpha, through high-affinity binding sites (Syrovets et al., Mol. Pharmacol. 2000; 58(1):71-81). Boswellic acid exerts antiproliferative properties on cancer cells with ability to induce apoptosis through activation of caspase-3/8/9 and PARP cleavage as demonstrated in a large number of various types of cancer cells including HT-29 cells (Liu et al., Carcinogenesis. 2002; 23(12):2087-93) human leukemia cells HL-60, K 562, U937, MOLT-4, THP-1 and brain tumor cells LN-18, LN-229 (Hostanska et al., Anticancer Res. 2002; 22(5):2853-62). Moreover, boswellic acids exert potent anti-inflammatory effects via blocking the leukotriene/5-lipoxygenase, a pathway that is central to the growth of cancer (Safayhi et al., J Pharmacol Exp Ther. 1997; 281(1):460-3; Abe and Yoshimoto, Nippon Yakurigaku Zasshi. 2004; 124(6):415-25; Sun et al., Carcinogenesis. 2006; 27(9):1902-8; Fan et al., J Altern Complement Med. 2005; 11(2):323-31). Due to the historical use of frankincense and the AHPA-BSH classification of this herb as a Class 1 herb, this could be the central to an herbal anti-cancer formulation (McGuffin, American Herbal Products Association's Botanical Safety Handbook CRC Pr Inc., 1997). Boswellia serrata extract is available and sold in capsule form with applicable suggested internal intake at approximately 400 mg (3× daily), with no side effects as of yet having been reported in the literature. Therefore, this herb can readily be incorporated into the anti-cancer specific CAM as described in this embodiment.

Again, there is very little scientific research regarding potential application of Bakuchi Seed (*Cyamopsis psoralioides*), although historical use includes treatment of leprosy, jaundice, infections, tumors and baldness. Bakuchi seed powder is available and marketed, without warnings or adverse side effects reported. Although this seed appears to be safe for oral consumption, the lack of information regarding its safety warrants further research. While our data supports bakuchi seed as a potent anti-cancer natural product, this ingredient to the formulation should be incorporated at relatively low dose.

Dichroa Root (*Dichroa febrifuga*) has historical use as an effective anti-malarial agent. While there are no documented research studies regarding applicable use to treat cancer, dichroa root is commonly sold and marketed with suggested use (5-10 grams/daily). While the data in this study show considerable promise for extract of this root as an anti-cancer agent, interestingly, there is little to no research investigating potential application of this herb, other than effects on immune function (Murata et al., J Nat. Prod. 1998; 61(6):729-33). Dichroa Root can be incorporated into the formulation however this component will require further research in assessing its safety and efficacy.

There is no scientific research pertaining to the use of Kanta Kari (*Solanum xanthocarpum*) describing anti-cancer properties. Kanta kari is commonly used in India for the treatment of asthma and respiratory infections of which its clinical and experimental use in animals is effective for intended purpose without side effects (Govindan et al., J Ethnopharmacol. 1999; 66(2):205-10; Govindan et al., Phytother Res. 2004; 18(10):805-9; Kar et al., J Ethnopharmacol. 2006 May 26; Epub ahead of print). Given that the use of this herb is commonly consumed in India for a wide variety of ailments without reported side effects, this herb has considerable promise. There are no known regulations regarding use of this herb, no reported side effects other than an active chemical constituent of this herb (salasodine) when isolated, could have anti-fertility effects (Gupta and Dixit, Indian J Exp Biol. 2002; 40(2):169-73).

While there are few prior research studies investigating the anti-cancer properties of *garcinia* Fruit (*Garcinia cambogia*), prenylated xanthones derived from the fruit of *garcinia mangostana* (mangosteen) are known to exert potent inhibitory effects on the development of preneoplastic lesions in mammary/colon (Jung et al., J Agric Food Chem. 2006 22; 54(6): 2077-82; Nabandith et al., Asian Pac J Cancer Prev. 2004; 5(4):433-8) and exert potent cytotoxic effects to mouth, leukemia, breast, gastric, lung, and liver cancer cell lines in vitro (Suksamram et al., Chem Pharm Bull (Tokyo). 2006; 54(3): 301-5; Ho et al., Planta Med. 2002; 68(11):975-9; Matsumoto et al., Biol Pharm Bull. 2003; 26(4):569-71). Known xanthones extracted from the *garcinia cambogia* fruit rind, such as gambogic acid mediate anti-cancer effects through downregulation of c-MYC mRNA expression/telomerase reverse transcriptase gene and initiate apoptosis contributing to the disrupting to both cell proliferation and immortalization of human cancer cells (Guo et al., Acta Pharmacol Sin. 2004; 25(6):769-74; Zhang et al., Bioorg Med. Chem. 200415; 12(2):309-17). In animals, administration of gambogic acid was found to reduce tumor growth of SMMC-7721 transplanted carcinoma (Guo et al., Acta Pharmacol Sin. 2004;

25(6):769-74). A second potent tumoricidal chemical derived from garginia cambogia is garcinol, a polyisoprenylated benzophenone capable of impairing unbridled cell proliferation by inhibiting nuclear histone acetyltransferases p300 and PCAF, also capable of initiating apoptotic signaling in HeLa cells (Balasubramanyam et al., J Biol. Chem. 2004; 279(32): 33716-26). Garcinol adversely impacts tumor cell proliferation, migration, cell adhesion and viability due to its ability to inhibit stress activated MAPK/ERK, PI3K/Akt, the phosphorylation of membrane focal adhesion kinase, ability to augment expression of BAX, caspase 2/3 activation, initiate release of cytochrome C, PARP-1 cleavage, this to be the case in diverse human cancer cell lines (Liao et al., J Cell Biochem. 2005; 96(1):155-69; Pan et al., J Agric Food Chem. 2001; 49(3):1464-74). In animals, the oral administration of garcinol effectively blocks 4-nitroquinoline 1-oxide chemically induced tongue squamous cell carcinoma/papilloma, preneoplastic lesions (Yoshida et al., Cancer Lett. 2005; 221(1):29-39) and azoxymethane—induced colon cancer (Tanaka et al., Carcinogenesis. 2000; 21(6):1183-9). Recommended dosages for oral intake of *garcinia cambogia* is estimated to be 3-6 tablets per day of 500-1000 mg *Garcinia cambogia* per tab. For this reason *garcinia* could yield a high fractional percent weight of the total composition of an anti-cancer based formulation. It is potent and well tolerated at significant doses.

Use of white sage (*Salvia apiana*) and similar plants inherent to the botanical genus Salvia date back to 1400 AD as a food preservative, flavoring, and medicinal agent to treat headaches, pains, indigestion, heart disease, colds and influenza. Alcohol extracts of sage demonstrate a diverse range of beneficial medicinal properties much attributed to inherent polyphenolics: rosmarinic acid, camphor and carnasol, yielding anti-inflammatory, antioxidant, anti-malarial, anti-bacterial and anti-fungal effects (Matsingou T C et al., J Agric Food Chem. 2003; 51(23):6696-701; Kamatou G P et al., J Ethnopharmacol. 2005 1; 102(3):382-90; Feres M et al., J Int Acad Periodontol. 2005; 7(3):90-6; Ninomiya K et al., Bioorg Med Chem. Lett. 2004; 14(8):1943-6; Sokovic M et al., Nahrung. 2002; 46(5):317-20). In animals, alcohol extracts of sage can be lethal to rodents when administered at very high concentrations equal to or above 3000 mg/kg (Eidi M et al., J Ethnopharmacol. 2005; 100(3):310-3) and the essential oil of sage under various seasonal conditions is known to have an LD50 at above 800 mg/kg in mice (Farhat G N et al., Toxicon. 2001; 39(10):1601-5). At lower dose, oral administration of sage tea in drinking water of rodents (approximately 10 mg/kg) was found safe and effective in providing hepatoprotective effects and a reduction in BHt induced lipid peroxidation in hepatocytes (Lima C F et al., Ethnopharmacol. 2005; 97(2):383-9). In humans, the administration of essential oil of sage has beneficial effects on memory, cognitive function, mood, and alertness (Tildesley N T et al., Physiol Behav. 2005; 83(5):699-709) with potential application for treatment of Alzheimer's disease (Perry N S et al., Pharmacol Biochem Behav. 2003; 75(3):651-9). Toxicity associated with sage is primarily associated with the oil of sage, inducing hypoglycemia, tachycardia, convulsions, muscle cramps and respiratory disorders (Gali-Muhtasib H et al., J Ethnopharmacol. 2000; 71(3):513-20). The Commission E has "approved the internal use of sage leaf for dyspeptic symptoms and excessive perspiration, and external use for inflammations of the mucous membranes of nose and throat with recommended dry leaf intake: 1-3 g, three times daily or Fluid extract 1:1 (g/ml): 1-3 ml, three times daily" (The Complete German Commission E Monographs: Therapeutic Guide to Herbal Medicines Lippincott Williams & Wilkins; 1998. Herbalgram online database). Sage is none the less classified as a AHPA-BSH Class 2b herb, not advised for long term use or during pregnancy, and not to exceed the recommended dose of 4-6 grams daily (McGuffin, American Herbal Products Association's Botanical Safety Handbook CRC Pr Inc., 1997). Given the extensive history regarding the beneficial use of sage in medicinal applications, and in light of adverse side effects with large doses, this herb shows promise, but its use should be restricted to suggested dose (Kennedy D O et al., Neuropsychopharmacology. 2006; 31(4):845-52).

Bushy Knotweed Rhizome (*Polygonum Cuspidatum*) is far from an endangered species, classified as an unwanted invasive, noxious weed which grows aggressively, survives in adverse climates and dominates ever expanding habitation and vegetative life, even to the point of creating an economic threat. Yet this is a plant that may offer superb anti-cancer properties. Previously, reported medicinal properties include its use as a potential cholesterol lowering agent (Park C S et al., Vascul Pharmacol. 2004; 40(6):279-84) antibacterial (Song J H et al., Arch Oral Biol. 2006) anti-viral/HIV (Chang J S et al., Antiviral Res. 2005; 66(1):29-34) estrogenic agent (Zhang C Z et al., J Ethnopharmacol. 2005 26; 98(3):295-300) and it contains a substance that is beneficial against neurological deficits and brain infarction associated with ischemia reperfusion injury (Cheng Y et al. Brain Res. 2006 July 24). Although the extract of this plant has not yet been examined for its anti-cancer properties, 3,4'-dimethoxy-5-hydroxystilbene which was obtained by methylation/acid hydrolysis of resveratrol-3-O-glucoside induces apoptosis in human promyelocytic leukemic HL-60 cells (Lee E B et al., Biol Pharm Bull. 2005; 28(3):523-6). Likewise, another compound inherent to the herb (resveratrol) is known to induce pro-apoptotic/antiproliferative effects on cancer cells through inhibition of nuclear factor-kappa B, COX-2 of which its oral administration at low dose was effective against 7,12-dimethylbenz(a)anthracene (DMBA) mammary carcinogenesis in female Sprague Dawley rats (Banerjee S et al., Cancer Res. 2002; 62(17):4945-54). Due to the promising results, regarding the potency of this plant extract on inducing cell death in blastoma cells, this herb may be beneficial in an anti-cancer herbal formulation.

The data identified gromwell root (*Lithospermum erythrorhizon*) (LER) as one of the highest ranked herbs. The use of LER in traditional chinese medicine is not typically used for cancer, but known to maintain the health of the heart and liver, "to cool and invigorate the blood", facilitate passage of stools and urine and its most common use is for treatment of skin boils, eczema and burns. The advised daily dose of this root is 3-9 grams per day, indicating its use at high concentrations has been used historically (Bensky et al., 2004). is classified under the Boraginaceae family (Borage), and its extract yields a very appealing red-purple pigment analogous to synthetic dyes purported for use in commercial cosmetics. These light sensitive pigments are attributable in large to shikonin naphthoquinones such as deoxyshikonin, shikonin, acetylshikonin, isobutylshikonin and beta-hydroxyisovalerylshikonin which varying in color according to pH. A large number of shikonin naphthoquinones are emerging as promising chemotherapy agents with ability to induce apoptosis in diverse range of cancer cells (Hou Y et al., Yakugaku Zasshi. 2006; 126:1383-6. Cui X R et al, Eur J Med. Chem. 2008; 43:1206-15).

Galbanum is a dark brown-yellow sticky resin with a distinct pungent odor classified under the botanical family Apiaceae (Carrot family). Galbanum was highly regarded historically, having been referenced in the bible and by ancient Egyptians as a holy anointing agent. Galbanum was one of the earliest drugs known to man, due to its diverse curative powers often associated with treatment of general pains, seizures, wounds, infections and inflammation. Today, the resin is used primarily as an odorant or flavoring agent associated with the fragrance of must (Bajgrowicz et al., 2003), where its medicinal value has been lost with time reflected by a lack of established research pertaining to this plant.

BRIEF SUMMARY OF INVENTION

The present invention describes a composition and method for treating/preventing cancer or to use as adjunct to chemotherapy. The formulation is comprised of a combination of (A) a quinone product: 2,3-dimethoxy-5-methyl-1,4-benzoquinone, ubiquinones (5-50), tocopheraol quinone or thymoquinone (B) a compound or combination of nutrients that augment mitochondrial oxidative phosphorylation such as riboflavin, FAD, FMN, coenzyme Q10, thiamin, biotin, pantothenate or lipoic acid and constituents required for ubiquinone synthesis including tyrosine, tetrahydrobiopterin (THB), vitamins B2, B6, B12, folate, niacin, vitamin C (C) substance(s) capable of inhibiting LDH such as 2',3,4'5,7-pentahydroxyflavone, epigallocatechin gallate, quercetin, citric acid, rosemary (Rosmarinus officinalis), black walnut (Juglans nigra), clove (Syzygium aromaticum), nutmeg (Myristica fragans), licorice root (Glycyrrhiza glabra), coriander (Coriandrum sativum), cinnamon (Cinnamomum cassia), ginger root (Zingiber officinale), Myrrh Gum (Commiphora molmol) and green tea (Camellia sinensis); (D) alkalizing agent(s) such as aloe vera, chlorella, wheat grass, apple cider vinegar, burdock root, kudzu root, alfalfa, barley grass, spirulina and parsley leaf, and calcium, magnesium, potassium or bicarbonate salts and (E) several potent anticancer herbs selected from the group consisting of wild yam (Dioscorea Villosa), beth root (Trillium Pendulum Root), Teasel Root (Dipsacus asper), Balm of Gilead Bud (Populus balsamifera), Frankincense (Boswellia carteri), Bakuchi Seed (Cyamopsis psoralioides), Dichroa Root (Dichroa febrifuga), Kochia Seed (Kochia scoparia), Kanta Kari (Solanum xanthocarpum), Teasel Root (Dipsacus asper), Sweet myrrh (Opopanax), gromwell root (Lithospermum erythrorhizon root), galbanum (Ferula galbaniflua), Garcinia Fruit (Garcinia cambogia), Mace (Myristica fragans), White Sage (Salvia apiana) and tumoricial plant derived constituents: gambogic acid, shikonin, diosmin or boswellic acid. (F) an antiproliferative herb selected from the group consisting of Speranskia Herb, (Speranskia tuberculata) or Goldenseal (Hydrastis Canadensis).

BRIEF DESCRIPTION OF THE DRAWINGS

FIG. 1 Summary of results—Re: Mazzio and Soliman, Biochem Pharmacol. 67:1167-84, 2004. The following schematic is a brief description summarizing the findings in this study. Briefly, the paper describes the function of ubiquinone (50) in augmenting the kinetic activity of mitochondrial complex II in cancer cells, while having no positive effect on mitochondrial respiration. On the other hand, riboflavin appears to control the kinetic activity of complex I, which drastically potentiates the rate of mitochondrial oxygen consumption through complex IV. These findings describe the inverse relationship between a reduction in mitochondrial oxygen consumption (ie. mitochondrial poisons), and anaerobic ambient conditions that foster enhanced glycolytic activity, leading to metabolic activation, glucose depletion and cell death by starvation. Conversely, a rise in ambient oxygen concentration or enhanced mitochondrial oxygen consumption (riboflavin) appears to disrupt glycolysis or glucose utilization. Further, neuroblastoma cells have the ability to thrive under completely anaerobic conditions (ie. in the presence of mitochondrial poisons such as MPP+, in the absence of $O_2$, or the removal of dissolved $O_2$ with dithionite) given that glucose supply is sustained. Briefly, our findings indicate that the mode of MPP+ toxicity in a blastoma cell model for the study of Parkinson's disease occurs through the propelling of anaerobic glucose metabolism leading to subsequent depletion of glucose supply and cell death by starvation. These findings may be relevant to the study of cancer as they demonstrate the dependency of malignant cells to derive ATP solely through substrate level phosphorylation and the adverse effects of optimized mitochondrial function on anaerobic glycolysis.

FIG. 2—The toxicity of selected plant extracts and 2',3,4'5,7-pentahydroxyflavone were previously determined on N-2A neuroblastoma cells prior to examination of their effects on kinetic activity of pyruvate kinase (PK) and LDH (data not shown). Briefly, the effects of experimental compounds on PK and LDH Type V, resembling that inherent to human cancer (Koukourakis et al., Br J Cancer. 2003; 89:877-85; Augoff and Grabowski. Pol Merkuriusz Lek 2004; 17:644-7; Nagai et al., Int J Cancer. 198815; 10-6; Evans et al., Biol. Chem. 1985; 260:306-14) were determined in pure isolated enzyme preparations. Briefly, PK Type III (from rabbit muscle [2.7.1.40]) was prepared in distilled water+HEPES (pH 7.5), at a concentration of 0.5 enzyme U/ml. Pyruvic acid was converted to lactate in the presence of LDH (from rabbit muscle, type V-S [EC 1.1.1.27]), at a concentration of 10 U/ml in the presence of adenosine, 2',5'-diphospahte (ADP) (1.5 mM), β-NADH (1 mM)±magnesium sulfate ($MgSO_4$) (5 mM). Experimental compounds were incubated with the enzyme solution for 10 minutes and addition of 1 mM phosphoenolpyruvate (PEP) prepared in distilled water started the reaction. Negative controls were established for all compounds tested. Enzyme activities were determined by spectrophotometric analysis using a UV spectrometer at 340 nm, by monitoring the oxidation of NADH. Experimental compounds that blocked the reaction through the PK/LDH cascade, were re-analyzed for LDH inhibition. LDH activity was achieved using an enzyme reaction mixture, minus PK or PEP, and starting the reaction with pyruvate (1 mM) prepared in buffered distilled water. Validation studies for LDH kinetic activity were established by monitoring the oxidation of NADH over time and concentration with dual detection quantifying lactic acid using a lactate oxidase based colorimetric enzymatic assay (Procedure No 735, Sigma Diagnostics, St. Louis, Mo.).

FIG. 5 (A-H) & FIG. 6. Some of the most potent tumoridal herbs from >700+ nutraceuticals that were screened. The data represent loss of cell viability after 24 H incubation at 37° C., and represent the Mean±S.E.M. . . . n=4

DETAILED DESCRIPTION OF THE PREFERRED EMBODIMENT

Figure 2A:
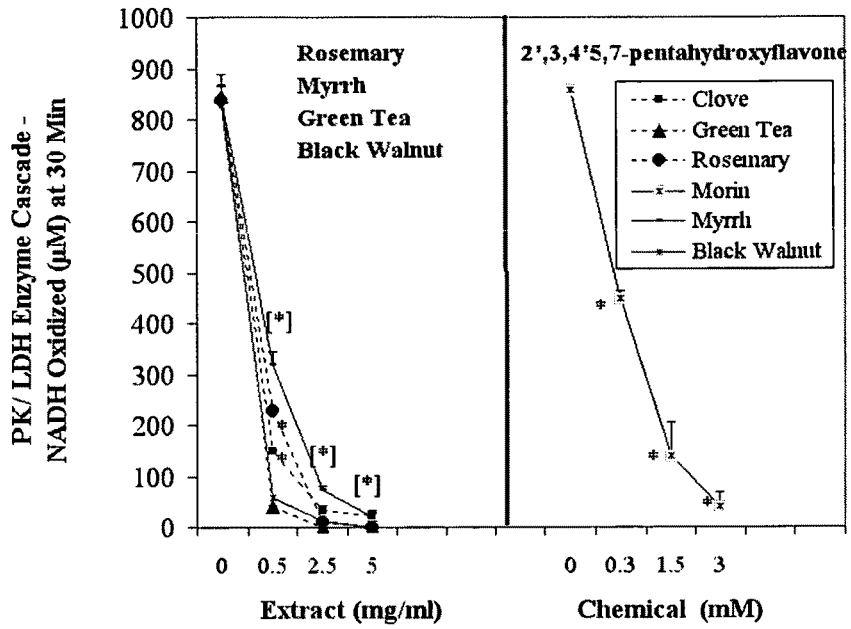
FIG. 2A describes the effect of tumoricidal plant extracts and 2',3,4'5,7-pentahydroxyflavone on inhibition of PK/LDH activity. The data represent reaction rate of NADH oxidation in the presence of enzyme/cofactor reagents+PEP (1 mM)±varying concentration of experimental compounds at 30 Min. The data are expressed as the Mean±S.E.M., (n=4). Significance of difference from the controls were determined by a one-way ANOVA, followed by a Tukey mean comparison post hoc test, [*] group P<0.001,*P<0.001.
Figure 2B:
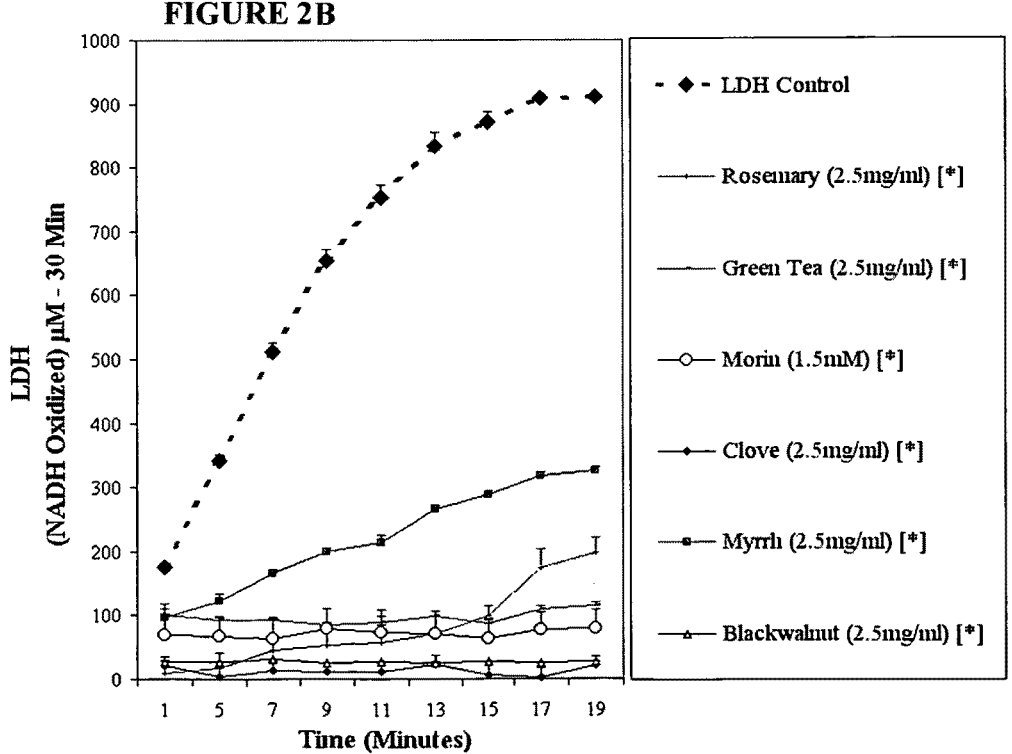
FIG. 2B describes the effect of tumoricidal plant-extracts and 2',3,4'5,7-pentahydroxyflavone on inhibition of LDH activity. The data represent reaction rate of NADH oxidation in the presence of enzyme/cofactor reagents+pyruvate (1 mM)±single level of experimental compound over time. The data are expressed as the Mean±S.E.M., (n=4). Significance of difference from the control was determined by a two-way ANOVA, [*] P<0.001.

The embodiment of the present invention describes a holistic chemotherapy agent for treatment/prevention of cancer in humans and animals. Briefly, ubiquiones, thymoquinone, tocopherol quinone, 2,3-dimethoxy-5-methyl-1,4-benzoquinone (ubiquinone (O)) herein termed "DMBQ" and the short chain ubiquinones are present to adversely target an unknown target causing collapse of anaerobic metabolism of tumor cells. The ubiquinones also play an important role in oxidative phosphorylation as they shuffle electrons to flavoprotein enzymes (requiring FMN prosthetic groups) and cytochromes, thereby translocating protons to generate a proton-motive force by which oxidative phosphorylation leads to aerobic production of ATP. Riboflavin, FAD and FMN in the formula serve to augment electron transport and the function of ubiquinone oxidoreductases, to boost $O_2$ utilization by the mitochondria (Mazzio and Soliman, Biochem Pharmacol. 67:1167-84, 2004; publication summary of FIG. 1. Agents that inhibit LDH-V also slow glucose metabolism and energy production required by tumor cells for survival (Koukourakis et al., Br J Cancer. 2003; 89:877-85; Augoff and Grabowski. Pol Merkuriusz Lek 2004; 17:644-7; Nagai et al., Int J Cancer. 198815; 10-6; Evans et al., Biol. Chem. 1985; 260:306-14), some of which are displayed in FIG. 2A,B.

Figure 3A:
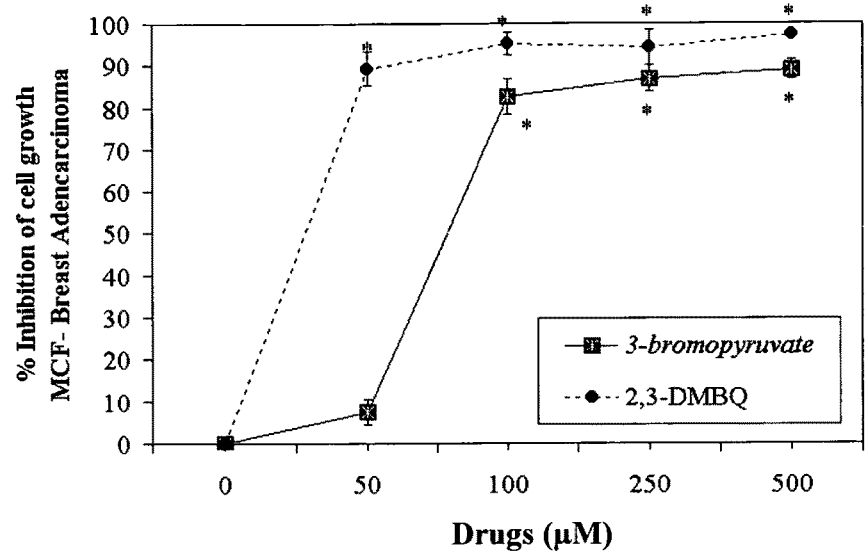
FIG. 3A describes the evaluation of 3-bromopyruvate (3-BP) versus 2,3-dimethoxy-5-methyl-1,4-benzoquinone (2,3-DMBQ) on growth inhibition of MCF-7 mammary carcinoma cells. Briefly, cells were grown in Eagles MEM medium with 20 mg insulin/ml and 10% calf serum and plated at 5' 104 cells in 24 well plates. Appropriate positive (tamoxifen) and negative (no drug) controls were maintained simultaneously. After 24 hour incubation, cells were trypsined and collected by centrifugation, re-suspended in fresh media and cells were counted using trypan blue dye on a hemocytometer. The data are expressed as the mean±S.E.M., n=3, and the significance of difference from the controls was determined by a one way ANOVA, followed by a Tukey mean comparison post hoc test (*=P<0.001).
Figure 3B:
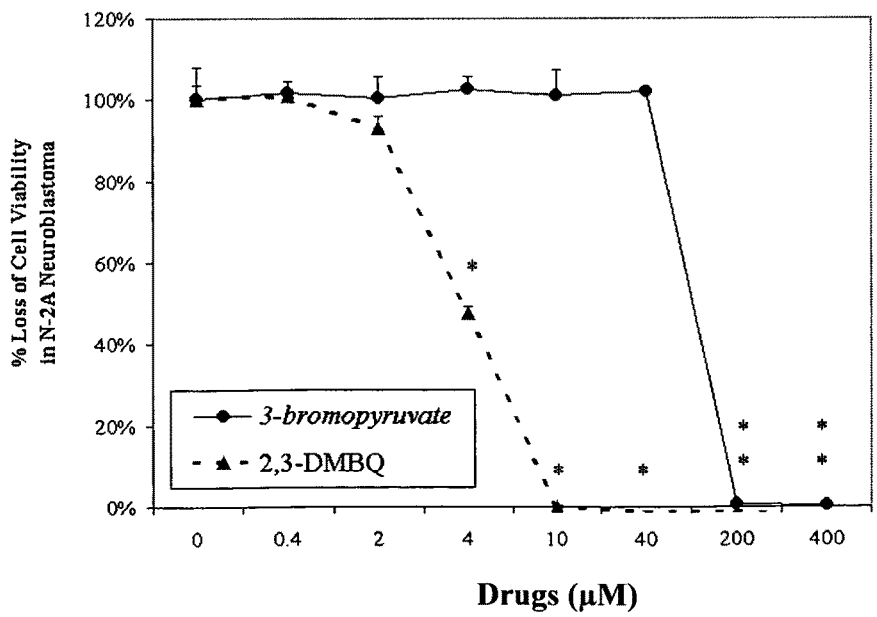
FIG. 3B represents the evaluation of 3-BP versus 2,3-DMBQ on cell viability in N2A neuroblastoma cell line. Briefly, the experimental media consisted of DMEM (without phenol red), supplemented with 1.8% FBS (v/v), penicillin (100 U/ml)/streptomycin (0.1 mg/ml), 4 mM L-glutamine and 2 µM sodium pyruvate. Cells were plated at approximately 0.5×106 cells/ml in 96 well plates. A stock solution of each experimental compound was prepared in HBSS containing 5 mM HEPES, adjusted to a pH of 7.4. After 24 hours incubation at 37° C. and 5% CO2/atmosphere almar blue indicator dye was used to assess cell viability. Quantitative analysis of dye conversion was measured on a microplate fluorometer—Model 7620-version 5.02, Cambridge Technologies Inc. with settings fixed at [550/580], [excitation/emission], wavelengths. The data are expressed as the mean±S.E.M., n=4, and the significance of difference from the controls was determined by a one way ANOVA, followed by a Tukey mean comparison post hoc test (*=P<0.001).

The toxicity of 2,3-dimethoxy-5-methyl-1,4-benzoquinone on neuroblastoma and MCF-7 cell line derived from the pleural effusion of a female patient with metastatic breast carcinoma are shown in (FIGS. 3A,B). The effects of DMBQ were >50× more toxic than bromopyruvate, which is currently considered a cancer breakthrough due to its lethal effects on certain types of tumors, with little observable toxic effects to the host (BBC News, Jul. 16, 2002).

Figure 4A:
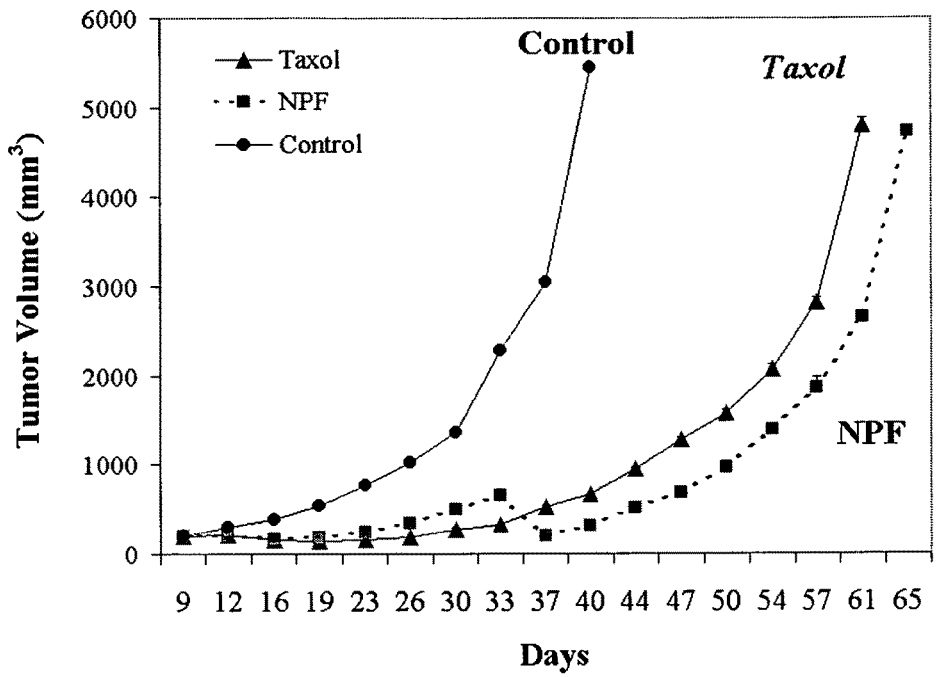
FIG. 4A describes the effect of a natural pharmaceutical formulation (NPF) on MD-MB-231 mammary carcinoma in Nu/Nu female mice. Briefly, 6 week old female Nu/Nu mice were kept in an autoclaved micro isolator cage, maintained under pathogen free conditions. The tumors were ascetically surgically removed and transferred to a sterile Petri dish containing RPMI-1640. The homogenate was centrifuged, pelleted, resuspended into a concentration of 10 million cells/ml and injected into the mammary fat pad. The tumors were established by day 9 after implant and treatment began. The formula was prepared in sterile saline, and administered by i.p. injection for 3 days and s.c for the next 3 days, stopping at day 15. Taxol—(24 mg/kg in 2% PEG 300, 8% cremophor CL an 80% sterile Saline) was administered i.v. intermittently up to day 19 (days 10,13,16 and 19). Since there were no signs of toxicity with the formulation, to gain greater understanding as to the effects of this drug, the dose was increased to 1.5× and 2× for two regimens implemented at day 35, and 37 of the tumor implantation. The data represents tumor volume estimation (mm3) and expressed as the mean±S.E.M., n=4, for treatment groups, with n=1 for the control.
Figure 4B:
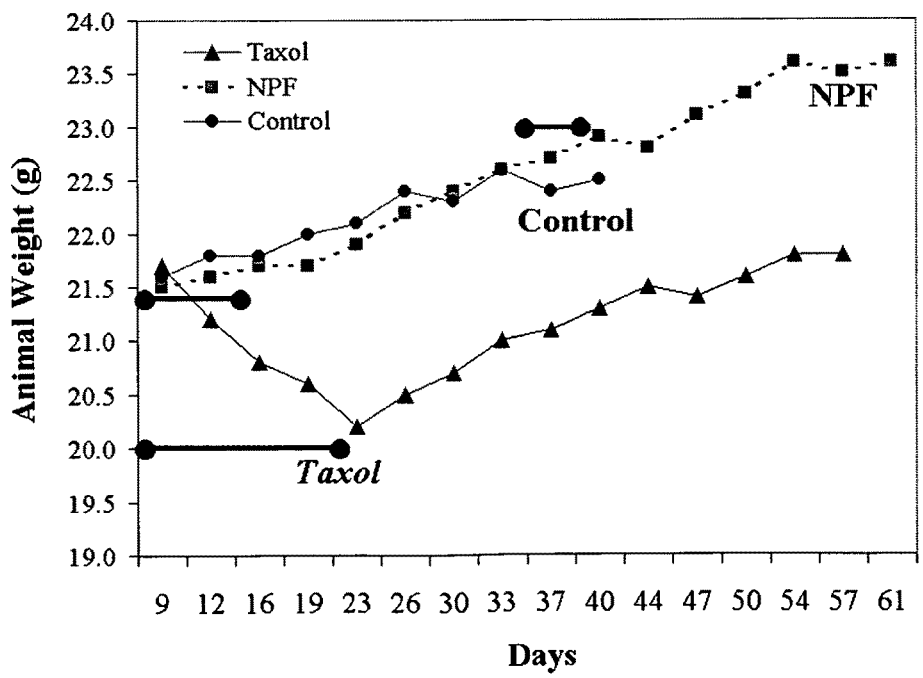
FIG. 4B describes the effect of a NPF treatment on weight loss, behavior and health. There were no deaths reported in the experiment due to toxicity. The control animals had a moderate weight gain within the acceptable limits for normal growth. There was a loss of weight with in the taxol treatment group. In a comparison chart, animals treated with the formulation showed no weight loss. The formulation was well tolerated by the animals in the dosing regimen, which showed no signs of toxicity, where food and water intake and excretory functions were normal. The animals showed no other behavioral changes. The data represents weight gain (g) and are expressed as the mean±S.E.M., n=4, for treatment groups, with n=1 for the control. Treatment period (!————!)

The tri-fold base formulation (riboflavin, 2,3-dimethoxy-5-methyl-1,4-benzoquinone and 2,3,4,5,7-pentahydroxyflavone) was further analyzed for efficacy against a breast cancer model in mice. The preliminary formulation was submitted to Kard Scientific (Boston, Mass.) for a small pilot study to determine efficacy against MD-MB-231 human mammary carcinoma in a xenograft model using Nu/Nu nude mice (FIGS. 4A,B). In this study, two treatment groups were established and consisted of the formulation and taxol®, both compared to a non-treated control. Both taxol® and the formulation showed a reduced tumor growth and growth latency in comparison to a vehicle control. Unlike taxol®, where there was weight loss observed during treatment, administration of the formulation accompanied no sign of toxicity, behavioral changes or weight loss in test animals. The formulation was well tolerated, where food and water intake, behavior and excretory functions were maintained at a normal level. The animals showed no other behavioral changes. The route of administration in this study was s.c. and i.p, indicating the formulation would be powerful if administered iv, like taxol. Further, the formulation is effective in its water-soluble form, yet readily modifiable to suit a large range of solubility's based on the number of side chain units associated with the quinoid base. This fulfills a current need to establish treatment that does not require emulsifying agents or solubilizing vehicles (ie cremaphor®), which can lead to further complications such as hypersensitivity reactions.

In addition to impeding anaerobic metabolism, addition of alkalizing substances create further vulnerability to cancer cell and addition of some of the most potent herbal constituents would instill a final lethal blow (FIG. 5 1-12) and FIG. 6. (Mazzio E, Soliman K F. In vitro screening for the tumoricidal properties of international medicinal herbs. Phytother Res. 2009 March;23(3):385-98).

In Total the Formulation Includes:

A) 2,3-dimethoxy-5-methyl-1,4-benzoquinone, ubiquinones (5-50), thymoquinone, or tocopherol quinone. This component also herein also termed and classified as the anaerobic inhibiting component "AIC (−)", B) a substance capable of augmenting mitochondrial oxidative phosphorylation herein termed "OXPHOS(+)", said OXPHOS (+) comprising riboflavin (vitamin $B_2$) and its derivatives, flavin adenine dinucleotide, flavin mononucleotide or analogs. The term OXPHOS (+) is further designated as a substance that serves to augment or contribute to the function of NADH:ubiquinone oxidoreductase (complex I), succinate dehydrogenase-CoQ oxoreductase (complex II), ubiquinol:cytochrome c oxidoreductase (complex III), cytochrome c oxidase (complex IV), ATP synthase (complex V), the Krebs cycle and mitochondrial respiration either directly or indirectly. These also include provision for metabolic precursors or compounds required for the biosynthesis of coenzyme $Q_{10}$, Krebs cycle or respiratory enzymes or the function thereof required for decarboxylation reactions/pyruvate dehydrogenase activity including: coenzyme $Q_{10}$, thiamin, biotin, pantothenate or lipoic acid and/or constituents required for ubiquinone synthesis including tyrosine, tetrahydrobiopterin (THB), vitamins B2, B6, B12, folate, niacin, vitamin C, pantothenic acid (Folkers et al., Biochem Biophys Res Commun 1996 244: 358-363) and ubiquinone metabolic precursors; para-hydroxybenzoate, para-hydroxycinnamate, para-hydroxyphenylpyruvate, para-hydroxyphenyllactate, polyprenyl-para-hydroxybenzoate, tyrosine, phenylalanine and isopentyl-diphosphate. The determination of compounds to be included in the OXPHOS (+) component, can be assessed by effects on the function of mitochondria/enzymes derived from any relevant source including but not limited to bacteria, animal, plant, yeast, mold or tumor.

C) 2,3,4,5,7-pentahydroxyflavone and/or a substance capable of inhibiting LDH, herein termed "LDH(−)". The term LDH(−) is further defined as any compound(s), substance(s) or agent(s) that can inhibit preferably LDH-5, the LDH inherent to cancer, as well as any other pertinent isoforms that can be used experimentally and relate to the LDH in cancer, including that derived from any source including but not limited to plant, bacteria, yeast, mold, fungus, animal or tumor. The LDH (−) component should be capable of inhibiting the LDH enzyme inherent to cancer or LDH-5 also termed "LDH-V", at concentrations that juxtapose tumoricidal effects indicating the mechanism of action involves inhibition of LDH. Other LDH inhibitors include 2',3,4'5,7-pentahydroxyflavone, epigallocatechin gallate, quercetin, citric acid, rosemary (*Rosmarinus officinalis*), black walnut (*Juglans nigra*), clove (*Syzygium aromaticum*), nutmeg (*Myristica fragans*), licorice root (*Glycyrrhiza glabra*), coriander (*Coriandrum sativum*), cinnamon (*Cinnamomum cassia*), ginger root (*Zingiber officinale*), myrrh gum (*Commiphora molmol*) and green tea (*Camellia sinensis*).

D) An alkalizing agent selected from the group consisting of *aloe vera, chlorella*, wheat grass, apple cider vinegar, burdock root, kudzu root, alfalfa, barley grass, spirulina and parsley leaf, and calcium, magnesium, potassium or bicarbonate salts.

E) Powerful anti-cancer herbs wild yam (*Dioscorea Villosa*), beth root (*Trillium Pendulum* Root), Teasel Root (*Dipsacus asper*), Balm of Gilead Bud (*Populus balsamifera*), Frankincense (*Boswellia carteri*), Bakuchi Seed (*Cyamopsis psoralioides*), Dichroa Root (*Dichroa febrifuga*), Kochia Seed (*Kochia scoparia*), Kanta Kari (*Solanum xanthocarpum*), Teasel Root (*Dipsacus asper*), Sweet myrrh (*Opopanax*), gromwell root (*Lithospermum erythrorhizon* root), galbanum (*Ferula galbaniflua*), Garcinia Fruit (*Garcinia cambogia*), Mace (*Myristica fragans*), White Sage (*Salvia apiana*) and tumoricial plant derived constituents: gambogic acid, shikonin, diosmin or boswellic acid.

F) Optionally one or more antiproliferative herbs selected from the group consisting of Speranskia Herb (*Speranskia tuberculata*) or Goldenseal (*Hydrastis Canadensis*) as listed in Further in depth, the incorporation of ubiquinone within the AIC (−) component also includes corresponding hydroquinones, ubichromenols, ubichromanols or synthesized/natural derivatives. Benzoquinones of this family are properly referred to as either "Coenzyme Qn" where n designates the number of isoprene units (also termed "prenyl") in the isoprenoid side chain, or alternatively, "ubiquinone (x)" where x designates the total number of carbon atoms in the side chain. The quinones of the coenzyme Q series differ in chemical structure and form a group of related, 2-3-dimethoxy-5-methyl-benzoquinones with variation in length of the polyisoprene side chain. The term "ubiquinone" is represented by the following base structure:

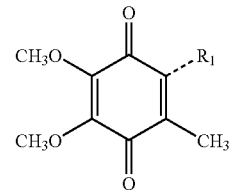

wherein $R_1$ is equal to or greater than 0 isoprene (3-methyl-2-butenyl) unit (s)

For example ubiquinone (5), which corresponds to the structure:

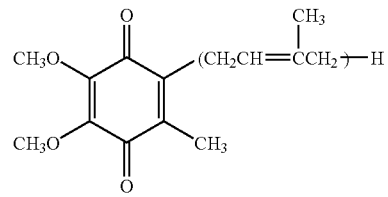

n = 1 wherein n is equal to the number of isoprene units

Coenzyme Q resembles vitamin K (base nucleus: 2-methylnaphthoquinone), the plastoquinones (base nucleus:2,3-dimethylbenzoquinone), tocopherolquinones (base nucleus: 2,3,5-trimethylbenzoquinone) and menoquinone (base nucleus: 2-methyl-4-naphthoquinone) in that it possesses a quinone ring nucleus attached to a hydrocarbon tail (IUPAC definitions—Eur. J. Biochem. 1975 53: 15-18). The ubiquinone component of the formulation may also include provision for the addition of plastoquinones or vitamin E/K quinones. Ubiquinones can further include any oxidized or reduced (ubiquinol) forms such as CoQ0, ubiquinone (O), ubiquinol/ubichromenol (0), CoQ1, ubiquinone (5), ubiquinol/ubichromenol (5), CoQ2, ubiquinone (10), ubiquinol/ubichromenol (10), CoQ3, ubiquinone (15), ubiquinol/ubichromenol (15), CoQ4, ubiquinone (20), ubiquinol/ubichromenol (20), CoQ5, ubiquinone (25), ubiquinol/ubichromenol (25), CoQ6, ubiquinone (30), ubiquinol/ubichromenol (30), CoQ7, ubiquinone (35), ubiquinol/ubichromenol (35), CoQ8, ubiquinone (40), ubiquinol/ubichromenol (40), CoQ9, ubiquinone (45), ubiquinol/ubichromenol (45), CoQ$_{10}$, ubiquinone (50), ubiquinol/ubichromenol (50) or any other derivative, analog, intermediate, precursor or pro-drug to these molecules.

Also included is the use of ubiquinones (0+) derivatives, analogues, intermediates, precursors and prodrugs. Examples include rearrangements, modification, substitutions of the methyl, methoxy or carbonyl groups or the isoprenoid side chain with substituents such as alkyl groups including branched, cyclic and straight chain, alkylene, alkoxy, alkenyl, alkaryl, alkynyl, acyl, acylamino, acyloxy, cycloalkyl, cycloalkenyl, haloalkyl, aryl substituents including phenyl, napthyl and substituted phenyl substituents; aralkyl substituents including benzyl and tolyl substituents; halogen substituents including fluoro, bromo, chloro substituents; oxygen substituents including hydroxy, lower alkoxy, ether, carboxyl and ester substituents; nitrogen substituents including nitrogen heterocycles, heteroaryls, amides, amines and nitriles; sulfur substituents including thiol, thioether, thioalkoxy, thioaryloxy and thioesters and aldehydes, ketones and aromatic hydrocarbons or hydrogen. In addition to altering the methyl, carbonyl group and/or the methoxy groups with the above noted substituents, addition, rearrangement, replacement or modification of substituents also provides ubiquinones that are also included within the scope of this invention. Accordingly, small changes resulting from modification of the substituents or benzoquinone nucleus for any improved functionality are included within the scope of the present invention. Ubiquinones utilized in the present invention may be isolated in nature or synthetically produced using any method including known to one skilled in the art, by way of example (Weinstock et al., Journal of Chem Eng Data 1967 12(1) 154-155; Sato et al, Chem. Abst. 78:471, 1993; U.S. Pat. No. 5,254, 590,10-19-1993, Malen et al; JP57021332, 02-04-1982, Kiso Yoshihis; U.S. Pat. No. 6,225,097, 05-01-2001, Obata et al; U.S. Pat. No. 6,103,488, 08-15-2000, Matsuda et al.; WO03/056024 12-27-2002 Yajima, K; JP57021332, 02-04-1982 Kiso Yoshihisa; DE3221506 12-08-1983, Doetz Karl Heinz; U.S. Pat. No. 6,545,184, 04-08-2003 Bruce Lipshutz and Paul Mollard; EP1354957, 10-22-2003, Matsuda Hideyuki et al; JP55159797, 12-12-1980, Hasegawa Yasuhiro), all of which are incorporated by reference. One of ordinary skill in the art will appreciate that changes may be made to the ubiquinone structure for improved functionality to form a derivative without taking away from the tumoricidal function thereof.

The OXPHOS (+) component comprising riboflavin, may also include its pharmaceutically acceptable salts and derivatives: flavin mononucleotide (FMN), flavin adenine dinucleotide (FMN) or any other synthesized or natural derivative. A riboflavin containing compound can also include compounds represented by the following base structure including its derivatives, intermediates, analogs, precursors and prodrugs including but not limited to 5-amino-6-(5'-phosphoribitylamino)uracil, 6,7-Dimethyl-8-(1-D-ribityl)lumazine, ribitol, lumichrome and 5,6-dimethylbenzimidazole. The term riboflavin is represented by the following base structure:

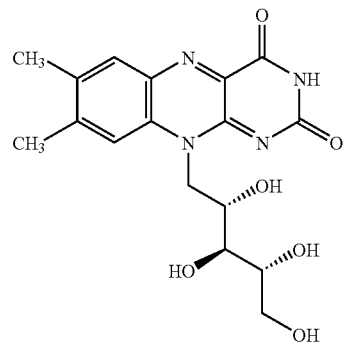 [SMILES: Cc1cc2nc3c(=O)[nH]c(=O)nc-3n(C[C@H](O)[C@H](O)[C@H](O)CO)c2cc1C]

where in the isoalloxazine ring system of riboflavin contains methyl groups at $C^7$ and $C^8$ and a ribityl group at $N^{10}$.

Examples of riboflavin derivatives can also include rearrangements, modifications, substitutions of the methyl, carbonyl, amino or ribityl group groups with additional substituents such as such as alkyl groups including branched, cyclic and straight chain, alkylene, alkoxy, alkenyl, alkaryl, alkynyl, acyl, acylamino, acyloxy, cycloalkyl, cycloalkenyl, haloalkyl, aryl substituents including phenyl, napthyl and substituted phenyl substituents; aralkyl substituents including benzyl and tolyl substituents; halogen substituents including fluoro, bromo, chloro substituents; oxygen substituents including hydroxy, lower alkoxy, ether, carboxyl and ester substituents; nitrogen substituents including nitrogen heterocycles, heteroaryls, amides, amines and nitriles; sulfur substituents including thiol, thioether, thioalkoxy, thioaryloxy and thioesters and aldehydes, ketones and aromatic hydrocarbons. Accordingly, small changes resulting from addition, modification, rearrangement or replacement of the substituents or base structure are included within the scope of the present invention. The term OXPHOS (+) includes also metabolic precursors or compounds required for the biosynthesis of coenzyme $Q_{10}$, Krebs cycle or respiratory enzymes or the function thereof such as required for decarboxylation reactions/pyruvate dehydrogenase activity including $CoQ_{10}$, thiamin, biotin, pantothenate or lipoic acid, constituents required for ubiquinone synthesis include tyrosine, tetrahydrobiopterin (THB), vitamins $B_2$, $B_6$, $B_{12}$, folate, niacin, vitamin C, pantothenic acid (Folkers et al., Biochem Biophys Res Commun 1996 244: 358-363) and the ubiquinone metabolic precursors include para-hydroxybenzoate, para-hydroxycinnamate, para-hydroxyphenylpyruvate, para-hydroxyphenyllactate, polyprenyl-para-hydroxybenzoate, tyrosine, phenylalanine and isopentyl-diphosphate.

The LDH (−) component can be morin (2,4,5,7-pentahydroxyflavone), which corresponds to the following structure and includes its derivatives, analogues and pro-drugs:

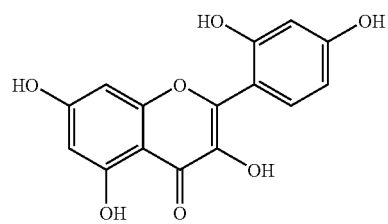 [SMILES: O=c1c(O)c(-c2ccc(O)cc2O)oc2cc(O)cc(O)c12]

The LDH (−) may also be any chemical, polyphenolic or plant extract capable of inhibiting preferably LDH-5, any isoform of LDH inherent to cancer tissue, or any other relevant isoform of LDH. And the LDH inhibitor component can be any synthesized or natural chemical, which is intended for the purpose of inhibiting LDH to treat any type of cancer. If the LDH inhibitor is a polyphenolic compound, it can further include phenolic acids (benzoic acid or cinnamic acid derivatives), benzofurans, chromones, coumarins, phenylacetic acids, phenols, phenylpropanoids, xanthones, stilbenes, quinones and flavonoids or corresponding derivatives, analogues and pro-drugs (Naczk and Shahidi, Chromatogr A. 2004 Oct. 29; 1054(1-2):95-111). If the LDH inhibitor is a flavonoid, it may be further characterized in that the structure is a aurone, flavone, isoflavone, flavanone, isoflavanone, catechin, flavan, flavanonol, chalcone, anthocyanidin, anthocyanin, proanthocyanidin, flavanol, flavonol, isoflavonol or biflavonoid moiety or corresponding derivatives, analogues and pro-drugs. One skilled in the art of bioflavonoids will recognize that a large number of compounds, both glycosides and aglycones, also fall within the scope of the present invention (Prasain et al., Free Radic Biol Med. 2004 Nov. 1; 37(9): 1324-50; Kris-Etherton et al., Am J. Med. 30, 71S-88S. 2002). And while morin was selected based on LDH specificity, other flavonoids such as epigallocatechin gallate and quercetin, as well as thiol oxidizing agents can effectively inhibit LDH, and may be substituted for/or combined with morin. It should be understood that the LDH (−) compound of the present invention can be administered in any pharmaceutically acceptable form including, salts, esters, ethers, derivatives and analogues thereof. The LDH (−) component may also be an extract of/or any form of/or any chemical constituent (s) inherent to rosemary (*Rosmarinus officinalis*), black walnut (*Juglans nigra*), clove (*Syzygium aromaticum*), nutmeg (*Myristica fragans*), licorice root (*Glycyrrhiza glabra*), coriander (*Coriandrum sativum*), cinnamon (*Cinnamomum cassia*), ginger root (*Zingiber officinale*), Myrrh Gum (*Commiphora molmol*) and green tea (*Camellia sinensis*). Either whole extracts or chemical constituents inherent to herbs can also be incorporated, substituted for/or combined as the LDH (−) component.

The buffering agent also termed "alkaline (+)" can include *aloe vera, chlorella*, wheat grass, apple cider vinegar, burdock root, kudzu root, alfalfa, barley grass, spirulina and parsley leaf, and calcium, magnesium, potassium, potassium or sodium bicarbonate salt as designated by the following structures:

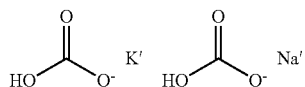

Herbal components can be prepared by any extraction or drying procedures. Any portion of the plant can be used, not limited to the root, seed, nut, stalk, bark, vegetable, fruit, hull, bud, leaf, flower, bulb or entire plant. Pure fresh herbs are typically dried at very low temperature, and macerated into an extract, comprised of one or more of the following: grain alcohol, distilled water, glycerine or vinegar. These also include any liquid, chemical, alcohol, lipophilic oil based solvents or acetone. Depending upon the strength of the herbal extract, dry herb menstrumm ratios can vary (w/v) between 1:5-4:5. Typically herbal extracts are stored in a sterile closed container (glass or suitable), in a warm dry area, away from light for about 0.5-2 weeks with intermittent stirring. The extract is then filtered to remove particulates and stored at a cool temperature in an amber container to prevent exposure to light.

The types of tumor treated by the formulation can be that of any organ, tissue or cell, including benign and malignant, and in humans or any species of animal. More specifically, the formulation may potentially be used to treat or prevent many types of cancers including but not limited to: cancer of the skin, breast, colon, kidney, bone, blood, lymph, stomach, gastrointestinal, ovary, prostate, liver, lung, head and neck, gallbladder, adrenal, brain, central nervous system, bronchial, eye, hypothalamus, parathyroid, thyroid, pancreas, pituitary, nose, sinus, mouth, endometrium, bladder, cervical, bile duct and specific types such as acute lymphoblastic leukemia, acute myeloid leukemia, AIDS related cancers, Burkitt's lymphoma, astrocytomas/gliomas and Hodgkin's lymphoma.

The term "pharmaceutically acceptable carrier" is defined as any safe material that acts as a vehicle for delivery including but not limited to: water, saline, starches, sugars, gels, lipids, waxes, paraffin derivatives, glycerols, solvents, oils, proteins, talc, glycols, electrolyte solutions, alcohols, gums, fillers, binders, cellulose, magnesium stearate, emulsifiers, humectants, preservatives, buffers, colorants, emollients, foaming agents, sweeteners, thickeners, surfactants, additives, solvents, lubricants or the like. The pharmaceutically acceptable carrier includes one or more compatible solid or liquid filler diluents or encapsulating substances that are suitable for administration to humans or animals.

The form of a pharmaceutically acceptable carrier used to deliver the treatment to a human or animal is all inclusive not limited to a cream, solid, liquid, powder, paste, gel, tablet, granule, foam, pack, ointment, aerosol, solvent, tablet, diluent, capsule, pill, drink, liposome, syrup, solution, suppository, emulsion, suspension, dispersion, food, bolus, electuary, paste or other bio-delivery system or agent. Formulations of the present invention embodiments include pharmaceutically acceptable carriers and delivery systems adapted for varying route of administration such as topical, enteral and parenteral including but not limited to: oral, rectal, nasal, vaginal, subcutaneous, intramuscular, intravenous, intratumor, intraperitoneal, intramammary, intraosseous infusion, transmucosal, transdermal, epicutaneous, intracutaneous, epidural, intrathecal, inhalation, opthalamic or other suitable route. Formulations for parenteral administration include aqueous and non-aqueous isotonic sterile solutions, which may contain antioxidants, oils, glycols, alcohols, buffers, bacteriostats, solutes, suspending agents, biodegradable time-release polymers, surfactants, preservatives and thickening agents. Formulations of the present invention adapted for oral administration may contain a predetermined quantity of the active ingredient and take the form of sprays, liquids, syrups, beverages, capsules, powders, granules, solutions, suspensions, tablets, food, lozenges or any other form in which the active ingredients are taken by mouth and absorbed through the alimentary canal. Enteral formulations may also incorporate the active ingredients with pharmaceutically acceptable carriers such as buffers, gums, surfactants, fillers, preservatives, bulking agents, colorants, diluents, flavoring agents, emulsifiers, sugars, oils, cellulose, gelatin, flour, maltodextrose, time release polymers and the like.

The term "therapeutically effective amount" is defined as an amount of one or more of the active ingredients that comprise this invention, administered to an animal or human at a dose such that efficacy of the treatment can bring about remission, prevention or halting of tumor growth or any other desired clinical result. The formulation may be presented in unit dosage form and may be prepared by any method well known in the art of pharmacy. The active ingredients of the formulation may be presented in liquid or solid, in ampoules or vials (preferably amber) or pill form and can be further incorporated with a pharmaceutically acceptable carrier, appropriate for the method of delivery as deemed appropriate by one skilled in the art.

The formulation can be administered alone or in combination to augment any chemotherapy agent(s) including but not limited to: acetogenins, actinomycin D, adriamycin, aminoglutethimide, asparaginase, bleomycin, bullatacin, busulfan, carmustine, carboplatin, chlorambucil, cisplatin, cyclophosphamide, cytarabine, dacarbazine, daunorubicin, doxorubicin, epirubicin, estradiol, etoposide, fludarabine, flutamide, fluorouracil, floxuridine, gemcitabine, glaucarubolone, hexamethylmelamine, hydroxyurea, idarubicin, ifosfamide, interferon, irinotecan, leuprolide, lomustine, mechlorethamine, melphalan, mercaptopurine, methotrexate, mitomycin, mitozantrone, mitotane, oxaliplatin, pentostatin, plicamycin, procarbazine, quassinoids, simalikalactone, steroids, streptozocin, semustine, tamoxifen, taxol, taxotere, teniposide, thioguanine, thiotepa, tomudex, topotecan, treosulfan, vinblastine, vincristine, vindesine and vinorelbine or mixtures thereof.

The formulation of substances that comprise this invention are not necessarily limited to definition by mechanism, since these agents may also meditate tumoricidal effects through other various means. On the other hand, the invention discloses a means through a mechanism to treat or prevent cancer by specifically and intentionally creating a formulation that combines one or more compounds classified under OXPHOS (+), AIC (−), LDH (−), Alkaline (+) and Proliferation (−). In addition to the formulation independent of mechanism, the mechanism of manipulating glucose metabolism in cancer cells through the described approach also comprises this invention, and also includes any or all type of modifications or methods to the development of a formula to achieve these means, that are obvious to one skilled in the art, but not described in the aforementioned and adhere to the scope of this invention.

What is claimed is:

1. A pharmaceutical composition useful for treating or reducing the risk of cancer comprising:
    a) frankincense (*Boswellia carteri*)
    b) at least one tumoricidal agent selected from the group consisting of beth root (*Trillium pendulum*root), galbanum (*Ferula galbaniflua*), and wild yam (*Dioscorea villosa*),
    c) at least one anti-proliferative herb comprising speranskia herb (*Speranskia tuberculata*) and;
    d) at least one lactic acid dehydrogenase inhibitor herein termed "LDH (−)" comprising at least one of cinnamon (*Cinnamomum cassia*) or 2',3,4',5,7-pentahydroxyflavone (morin), and
    e) a pharmaceutically acceptable carrier
    wherein the total amount of component a) is 5-20% by wt of the total composition, the total amount of component b) is 5-20% by wt of the total composition, and wherein component c) is present in a total amount of up to 8% by wt of the total composition.

2. The composition according to claim 1, wherein said pharmaceutically acceptable carrier comprises one or more selected from the group consisting of water, saline, starches, sugars, gels, lipids, waxes, glycerol, solvents, oils, liquids, proteins, glycols, electrolyte solutions, alcohols, stabilizers, fillers, binders, emulsifiers, humectants, preservatives, buffers, colorants, emollients, foaming agents, sweeteners, thickeners, surfactants, additives, solvents, and mixtures thereof.

3. The composition according to claim 2, wherein said pharmaceutically acceptable carrier is suitable for oral, external, or injectable administration and is in the form of a solid, liquid, powder, paste, gel, tablet, granule, foam, pack, aerosol, solvent, diluent, capsule, pill, drink, tea, liposome, syrup, solution, suppository, emulsion, enema, suspension, dispersion, food, or mixtures thereof.

4. The composition according to claim 1 wherein the total amount of said LDH (−) is 5-15% by wt of the total composition.

5. The composition of claim 1 wherein said LDH (−) further comprises one or more selected from the group consisting of gromwell root (*Lithospermum erythrorhizon* root), epigallocatechin gallate, quercetin, rosemary (*Rosmarinus officinalis*), citric acid, black walnut (*Juglans nigra*), clove (*Syzygium aromaticum*), nutmeg (*Myristica fragans*), licorice root (*Glycyrrhiza glabra*), coriander (*Coriandrum sativum*), ginger root (*Zingiber officinale*), myrrh gum (*Commiphora molmol*), and green tea (*Camellia sinensis*).

6. The composition of claim 1 wherein said tumoricidal agent further comprise one or more selected from the group consisting of teasel root (*Dipsacus asper*), bakuchi seed (*Cyamopsis psoralioides*), kanta kari (*Solanum xanthocarpum*), bushy knotweed rhizome (*Polygonum cuspidatum*), garcinia fruit (*Garcinia cambogia*), white sage (*Salvia apiana*), balm of gilead bud (*Populus balsamifera*), gambogic acid, and diosmin.

7. A method of inhibiting metastasis of cancer in a host, the method comprising administering to a host in need of cancer treatment an amount of the composition of claim 1 effective to inhibit metastasis of the cancer.

* * * * *

UNITED STATES PATENT AND TRADEMARK OFFICE
CERTIFICATE OF CORRECTION

PATENT NO. : 8,802,161 B2  
APPLICATION NO. : 12/657903  
DATED : August 12, 2014  
INVENTOR(S) : Elizabeth Anne Mazzio and Karam F. Soliman Page 1 of 1

It is certified that error appears in the above-identified patent and that said Letters Patent is hereby corrected as shown below:

In the Specification

Column 1, line 20, please amend as follows:

This invention was made with government support under RCMI G12 RR 03020 which was awarded by the National Institutes of Health. The government has certain rights in the invention.

Signed and Sealed this  
Twenty-seventh Day of October, 2015

Michelle K. Lee  
*Director of the United States Patent and Trademark Office*